US007812142B2

(12) United States Patent
Sasson et al.

(10) Patent No.: US 7,812,142 B2
(45) Date of Patent: Oct. 12, 2010

(54) PENTOSE DERIVATIVES AS ANTI-HYPERGLYCEMIC DRUGS

(75) Inventors: Shlomo Sasson, Jerusalem (IL); Erol Cerasi, Jerusalem (IL); Arie Gruzman, Jerusalem (IL); Joshua Katzhendler, Jerusalem (IL)

(73) Assignees: Yissum Research Development Company of the Hebrew University of Jerusalem, Jerusalem (IL); Hadasit Medical Research Services and Development Ltd., Jerusalem (IL)

( * ) Notice: Subject to any disclaimer, the term of this patent is extended or adjusted under 35 U.S.C. 154(b) by 1371 days.

(21) Appl. No.: 11/109,907

(22) Filed: Apr. 19, 2005

(65) Prior Publication Data

US 2005/0277599 A1 Dec. 15, 2005

Related U.S. Application Data

(63) Continuation of application No. PCT/IL03/00852, filed on Oct. 20, 2003.

(30) Foreign Application Priority Data

Oct. 21, 2002 (IL) .................................... 152397

(51) Int. Cl.
| | |
|---|---|
| A61K 31/7004 | (2006.01) |
| A61K 31/7008 | (2006.01) |
| A61K 31/7028 | (2006.01) |
| C07H 5/06 | (2006.01) |
| C07H 5/10 | (2006.01) |
| C07H 9/04 | (2006.01) |
| C07H 15/04 | (2006.01) |
| C07H 15/10 | (2006.01) |

(52) U.S. Cl. .................... 536/1.11; 514/23; 514/24; 514/25; 536/4.1; 536/17.2; 536/17.5; 536/18.3; 536/18.7; 536/54

(58) Field of Classification Search ........................ None
See application file for complete search history.

(56) References Cited

U.S. PATENT DOCUMENTS

| | | | | |
|---|---|---|---|---|
| 4,187,121 | A * | 2/1980 | Herold et al. | 134/26 |
| 4,315,921 | A * | 2/1982 | Yoshikumi et al. | 514/42 |
| 4,420,486 | A * | 12/1983 | Ohyama et al. | 514/375 |
| 4,966,890 | A * | 10/1990 | Gillespie | 514/25 |
| 5,432,163 | A | 7/1995 | Akhtar et al. | 514/25 |
| 5,468,734 | A | 11/1995 | Seri et al. | 514/23 |
| 5,604,206 | A * | 2/1997 | Paradies | 514/23 |
| 6,159,485 | A * | 12/2000 | Yu et al. | 424/401 |
| 6,329,344 | B1 | 12/2001 | Arora et al. | 514/25 |
| 6,809,115 | B2 * | 10/2004 | Katz et al. | 514/505 |
| 2004/0166126 | A1 * | 8/2004 | Cannell et al. | 424/401 |

FOREIGN PATENT DOCUMENTS

| | | | |
|---|---|---|---|
| WO | WO 01/51058 A1 | 7/2001 | |
| WO | WO 01/54702 | * | 8/2001 |

OTHER PUBLICATIONS

Slverman, The Organic Chemistry of Drug Design and Drug Action, published 1992 bt Academic Press, pp. 19-21.*
Wanner et al., "Studies in the Spectroscopic Synthesis of Sebanimide. Synthesis of 4-saccharidalglutarimides" Heterocycles (1984) vol. 22, No. 7, pp. 1483-1487.*
Merriam-Webster's Collegiate Dictionary, Tenth Edition, published 1998 by Merriam-Webster, Incorporated, p. 924.*
Martin et al., "D-Xylose Derivative Liquid Crystals" Journal of Thermal Analysis and Calorimetry (2001) vol. 63 pp. 339-344.*
Reist et al., "Potential Anticancer Agents. LVII. Synthesis of Alkylating Agents Derived from 6-amino-6-deoxy-D-glucose and 5-amino-5-deoxy-D-ribose" (1961) vol. 26, pp. 2821-2827.*
Wolfrom et al., "2-amino-2-deoxy-L-xylose" Journal of Organic Chemistry (1964) vol. 29, pp. 1479-1480.*
Clayton et al. "5-Thio-D-Ribopyranose" Carbohydrate Research (1973) vol. 27, pp. 89-95.*
Potgieter et al., "The Synthesis of Certain Benzylidene Derivatives of D-Ribose and Ribitol" Journal of Organic Chemistry (1961) vol. 26 pp. 3934-3938.*
Ness et al., "Derivatives of L-Xylose" Journal of the American Chemical Society (1952) vol. 74 pp. 5341-5343.*
Remington: The Science and Practice of Pharmacy, Twentieth Edition, published 2000 by Lippincott Williams and Wilkins, ed. By Gennarro et al., pp. 858-863.*
Aspinall et al., "Gas-Liquid Partition Chromatography of Methylated and Partially Methylated Methyl Glycosides" (1963) pp. 1676-1680.*
Grindley, "Kinetic benzylidenation. Part II Rearrangement of the kinetic products from benzylidenation of aldose diethyl dithiocetals" Canadian Journal of Chemistry (1986) vol. 64 No. 12, pp. 2397-2403.*
Kuszmann et al., "O-Benzylidene derivatives of D-arabinose diethyl and dipropyl dithioacetal" Aust. J. of Chem. (1996) vol. 49 pp. 273-280.*
Mukherjee et al., "3-Deoxy-1-xylose" Journal of the Chemical Society (1947) pp. 969-973.*
Pitorvsky et al., "Synthesis of 4-O-methyl-D-lyxose" Bulletin des Societes Chimiques Belges (1964) vol. 73 No. 11-12, pp. 969-975.*
Provencher et al., "Five-Membered Ring Azasugars as Potent Inhibitors" Bioorganic & Medicinal Chemistry (1994) vol. 2 No. 11, pp. 1179-1188.*

(Continued)

Primary Examiner—Eric S Olson
(74) Attorney, Agent, or Firm—Winston & Strawn LLP

(57) ABSTRACT

The present invention relates to pentose and pentose derivatives that are effective at increasing glucose transport in a non-insulin dependent manner, and to uses thereof for a) treating and/or preventing hyperglycemia; b) treating and/or preventing the complications of hyperglycemia; c) treating diabetes; d) increasing the rate of cellular glucose transport; e) increasing the rate of cellular glucose uptake; f) improving the ability of a subject to metabolize glucose; g) treating daily blood glucose fluctuations; h) reducing blood sugar levels; i) reducing the dosage of anti-diabetic medication needed for treatment of diabetes. The present invention further provides novel pentose derivatives having beneficial properties in terms of pharmacokinetics, to pharmaceutical compositions comprising these novel compounds and uses thereof.

33 Claims, 20 Drawing Sheets

OTHER PUBLICATIONS

Rao et al., "The reduction of benzylidene derivatives of pentose diethyl dithioacetals with lithium aluminium hydride-aluminium trichloride" Carbohydrate Research (1991) vol. 218 pp. 83-93.*

Rollin et al., "Synthesis of (6z)-cis-9S,10R-epoxyheneicosene, a component of the ruby tiger moth pheromone" Tetrahedron (1986) vol. 42. No. 13, pp. 3479-3490.*

Veloo et al., "Stereoselective formation of tetrahydrofurans during allyltrimethylsilane additions to L-xylose derivatives" Tetrahedron (1992) vol. 48 No. 25, pp. 5301-5316.*

Mobasheri et al., Glucose transport and metabolism in chondrocytes: a key to understanding chondrogenesis, skeletal development and cartilage degradation in osteoarthritis. Histol. Histopathol. (2002) vol. 17 No. 4, abstract.*

Moses, "Historical highlights and unsolved problems in glycogen storage disease type 1" European Journal of Pediatrics (2002) vol. 161, pp. S2-S9.*

Wright et al., "Molecular Basis for Glucose—Galactose Malabsorption" Cell Biochemistry and Biophysics (2002) vol. 36, pp. 115-121.*

Cerasi, E. "Aetiology of Type II Diabetes", Textbook of Diabetes ($2^{nd}$ edition) J. Pickup and G. Williams, Eds.(1997) Blackwell Science, Oxford.

Srikanta, S. et al., Type I Diabetes Mellitus in Monozygotic Twins: Chronic Progressive Beta Cell Dysfunction, American College of Physicians, Annals. of Internal. Medicine, vol. 99, pp. 320-326 (1983).

Cerasi, E. et al., "Plasma-Insulin Response to Sustained Hyperglycaemia Induced by Glucose Infusion in Human Subjects", Preliminary Communications, The Lancet, pp. 1359-1361 (1963).

Cerasi, E. et al., "The Plasma Insulin Response to Glucose Infusion in Healthy Subjects and in Diabetes Mellitus", Acta Endocrinologica, vol. 55, pp. 278-304 (1967).

Cerasi, E. et al., ""What Is Inherited-What Is Added" Hypothesis for the Pathogenesis of Diabetes Mellitus", Acta Endocrinologica, vol. 16, No. 9, pp. 615-627 (1967).

Genuth, S, "Plasma Insulin and Glucose Profiles in Normal, Obese, and Diabetic Persons", Annals. of Internal. Medicine, vol. 79, No. 6, pp. 812-822 (1973).

Leahy, J. L. et al., "Chronic Hyperglycemia Is Associated With Impaired Glucose Influence on Insulin Secretion", Journal of Clinical Invest., vol. 77, pp. 908-915 (1986).

Nesher, R., et al., "Interaction Between Genetic and Dietary Factors Determines β-Cell Function in .Psammomys obesus, an Animal Model of Type 2 Diabetes", Diabetes, vol. 48, pp. 731-737 (1999).

Cerasi, E. et al., "The Islet in Type 2 Diabetes: Back to Center Stage", Editorial, Diabetes 50 Supplement, pp. S1-S3 (2001).

Garvey, W.T. et al., "The Effect of Insulin Treatment on Insulin Secretion and Insulin Action in Type II Diabetes Mellitus", Diabetes, vol. 34, pp. 222-234 (1985).

Sasson, S. et al., "Substrate Regulation of the Glucose Transport System in Rat Skeletal Muscle Characterization and Kinetic Analysis in Isolated Soleus Muscle and Skeletal Muscle Cells in Culture", The Journal: Biological Chemistry, vol. 261, No. 36, pp. 16827-16833 (1986).

Sasson, S. et al., "In Vitro Autoregulation of Glucose Utilization in Rat Soleus Muscle", Diabetes, vol. 36, pp. 1041-1046 (1987).

Savage, P.J. et al, "Normalization of Insulin and Glucagon Secretion in Ketosis-Resistant Diabetes Mellitus with Prolonged Diet Therapy", Journal of Clinical Endocrinological and Metabolism, vol. 49, No. 6,, pp. 830-833 (1979).

Wertheimer, E. et al., "Regulation of Hexose Transport in $L_8$ Myocytes by Glucose: Possible Sites of Interaction" Journal of Cellular Physiology, vol. 143, pp. 330-336 (1990).

Walker, P. S. et al., "Glucose Transport Activity in L6 Muscle Cells Is Regulated by the Coordinate Control of Subcellular Glucose Transporter Distribution, Biosynthesis, and mRNA Transcription", Journal of. Biological Chemistry, vol. 265, pp. 1516-1523 (1990).

Mason, Anne B., "Mutagenesis of the Aspartic Acid Ligands in Human Serum Transferrin; Lobe-Lobe Interaction and Conformation as Revealed by Antibody, Receptor Binding and Iron-Release Studies", Biochemistry Journal, vol. 330, pp. 35-40 (1998).

Greco-Perotto, R. et al., "Glucose Regulates Its Transport in $L_8$. Myocytes by Modulating Cellular Trafficking of the Transporter GLUT-1", Biochemistry Journal, vol. 286, pp. 157-163 (1992).

Klip, A. et al., "Regulation of Expression of Glucose Transporters by Glucose" A Review of Studies In Vivo and in Cell Cultures, The FASEB Journal, vol. 8, pp. 43-53, (1994).

Mathoo, J. M.R. et al., "Opposite Effects of Acute Hypoglycemia and Acute Hyperglycemia on Glucose Transport and Glucose Transporters in Perfused Rat Skeletal Muscle", Diabetes, vol. 48, pp. 1281-1288 (1999).

Yki-Jarvinen, H., "Acute and Chronic Effects of Hyperglycaemia on Glucose Metabolism", Diabetologia, vol. 33, pp. 579-585 (1990).

Demetrakopoulos, G. E. et al., "D-Xylose and Xylitol: Previously Unrecognized Sole Carbon and Energy Sources for Chick and Mammalian Cells" Biochemical and Biophysical. Research Communications, vol. 72, pp. 1169-1178 (1976).

McCormick, D. B. et al., "The Conversion In Vivo of Xylitol to Glycogen Via the Pentose Phosphate Pathway", Journal of. Biological Chemistry, vol. 226, pp. 451-461 (1958).

Metzger, R. et al., "A Study of Glucose and Xylose Oxidation Catalyzed by the Glucose-6-Phosphate Dehydrogenase of Rat Liver Cytosol", Archives of. Biochemistry and Biophysics, vol. 149, pp. 102-109(1972).

Doiron, B. et al., "Transcriptional Glucose Signaling through the Glucose Response Element Is Mediated by the Pentose Phosphate Pathway", Journal of. Biological Chemistry, vol. 271, pp. 5321-5324 (1996).

Brinkman, T. et al., "Recognition of Acceptor Proteins by UDP-$_D$-xylose Proteoglycan Core Protein β-$_D$-Xylosyltransferase" Journal of. Biological Chemistry, vol. 272, No. 17, pp. 11171-11175 (1997).

Mourrieras, F. et al., "Induction of Fatty Acid Synthase and S14 Gene Expression by Glucose, Xylitol and Dihydroxyacetone in Cultured Rat Hepatocytes Is Closely Correlated With Glucose 6-Phosphate Concentrations", Biochemistry Journal, vol. 326, pp. 345-349 (1997).

Nishimura, Met al., "Purification and Characterization of a Novel Xylulose 5-Phosphate-activated Protein Phosphatase Catalyzing Dephosphorylation of Fructose-6-phosphate,2- kinase:Fructose-2,6-bisphosphatase", Journal of. Biological Chemistry, vol. 270, No. 44, pp. 26341-26346 (1995).

Sasson, S. et al., "Enzymatic Assay of 2-Deoxyglucose 6-Phosphate for Assessing Hexose Uptake Rates in Cultured Cells", Analytical. Biochemistry, vol. 215, pp. 309-311 (1993).

Bollenback, G. N., "Glycosidation [84] Methyl α-$_D$-Glucopyranoside Reaction of $_D$-Glucose With Methanol in the Presence of a Cation-Exchange Resin", In Methods in Carbohydrate Chemistry, vol. 2 (Whistler, R. L. and Wolfrom, M. L., eds.), pp. 326-331, Academic Press, New York (1963).

Bowering, W. D. S. et al., "An Alternative Synthesis of 2-0-Methyl-$_D$-Xylose", Can. J. Chem., vol. 36, pp. 283-284 (1958).

Levine, P. et al., "3-Methyl Xylose and 5-Methyl Xylose", Journal of. Biological Chemistry, vol. 102, No. 317, pp. 331-346 (1933).

Takeo, K. et al.,"A Facile synthesis of 4-O-allyl-$_D$-Xylopyranose and Its Use in the Preparation of Xylo-oligosaccharides", Carbohydrate Research, vol. 224, pp. 311-318 (1992).

Curtis, G. et al., "The Synthesis of 3-O-β-$_D$-Xylopyranosyl-$_D$-Xylose and the Recharacterization of Some Benzylidene Derivatives of $_D$-Xylose", Can. J. Chem. 38, pp. 1305-1315 (1960).

Ferrier, R. et al., "The Acid-Catalysed Condensation of $_D$-Xylose With Benzaldehyde in the Presence of Alcohols. Two Diastereoisomeric 1,2:3,5-D1-O-Benzylidente-α-$_D$-Xylofuranoses", Carbohydrate Research, vol. 5, pp. 132-139 (1967).

Seeberger, P. et al., "Oxidative Formation of Phosphorodithioates Via H-Phosphonodithioates", Tetrahedron Letters., vol. 36, No. 5, pp. 695-698 (1995).

Zalipsky, S., "Functionalized Poly(ethylene glycol) for Preparation of Biologically Relevant Conjugates", Bioconjug. Chem., vol. 6, pp. 150-165 (1995).

Andrews, W.J. et al., "Insulin Therapy in Obese, Non-Insulin-Dependent Diabetes Induces Improvements in Insulinaction and Secretion That Are Maintained for Two Weeks After Insulin Withdrawal", Diabetes, vol. 33, pp. 634-642 (1984).

Nesher, R., et al., "Insulin Deficiency and Insulin Resistance in Type 2 (Non-Insulin-Dependent) Diabetes: Quantitative Contributions of Pancreatic and Peripheral Responses to Glucose Homeostasis", European Journal of Clinical Investigation, vol. 17, pp. 266-274 (1987).

Revers, R. et al., "Influence of Hyperglycemia on Insulin's In Vivo Effects in Type II Diabetes", The American Society for Clinical Investigation Inc., vol. 73, pp. 664-672 (1984).

Olefsky, J. M. et al., "Mechanisms of Insulin Resistance in Obesity and Noninsuin-Dependent (Type II) Diabetes", American Journal of Medicine, vol. 70, pp. 151-168 (1981).

Nesher, R., et al., "Interaction Between Genetic and Dietary Factors Determines β-Cell Function in *Psammomys obesus,* an Animal Model of Type 2 Diabetes", Diabetes, vol. 48, No. 4, pp. 731-737 (1999).

DeFronzo, R. et al., "Hepatic and Peripheral Insulin Resistance: A Common Feature of Type 2 (Non-Insulin-Dependent) and Type 1 (Insulin-Dependent) Diabetes Mellitus", Diabetologia, vol. 23, pp. 313-319 (1982).

Ishac Edward J.N. et al., "Inhibition of Exocytotic Noradrenaline Release by Presynaptic Cannabinoid $CB_1$ Receptors on Peripheral Sympathetic Nerves", British Journal of Pharmacology, vol. 118, pp. 2023-2028 (1996).

* cited by examiner

OIL-INJECTED     EH-36 INJECTED

3-O-Methylxylopyranoside
EH-19

2,4:3,5-Di-O-benzalidene-D-xylose-diethyl-dithioacetal
EH-36

3-O-Ethylxylopyranose
EH-103

2,4-O-benzalidene-D-xylose-diethyl-dithioacetal
EH-40

3-O-Propylxylopyranose
EH-114

3-O-methyl-2,4-O-benzalidene-D-xylose-diethyl-dithioacetal
EH-169

1,3-Di-O-Methylxylopyranoside
EH-101

Di-4-(1-O-methyl-a-xylopyranoside)-phosphoryl-O-methyl-PEG
EH-109

OS-1B

3-Phenyl-9-propoxy-2,4,7-trioxa-bicyclo[3.3.1]nonan-6-ol

OS-1A

2-Phenyl-7-propoxy-tetrahydro-[1,3]dioxolo[4,5-b]pyran-6-ol

PENTOSE DERIVATIVES AS ANTI-HYPERGLYCEMIC DRUGS

CROSS-REFERENCE TO RELATED APPLICATIONS

This application is a continuation of International application PCT/IL2003/000852 filed Oct. 20, 2003, the entire content of which is expressly incorporated herein by reference thereto.

FIELD OF THE INVENTION

The present invention relates to the use of pentoses and pentose derivatives for the treatment of hyperglycemia by increasing glucose transport in a non-insulin dependent manner, and it further relates to novel pentose derivatives having beneficial properties in terms of pharmacokinetics, to pharmaceutical compositions comprising these novel compounds and uses thereof.

BACKGROUND OF THE INVENTION

Diabetes mellitus is one of the major diseases in the Western world, afflicting mostly the elderly population (it is estimated that 7% of men and 9% of women over the age of 65 years have diabetes mellitus). Diabetes mellitus is a complex set of diseases that are characterized by high blood glucose levels (hyperglycemia) and altered carbohydrate, lipid and protein metabolism leading to clinical complications such as vascular disorders, eye disorders such as retinopathy, glaucoma and cataracts, nephropathy, diabetic neuropathy and a variety of micro- and macrovessel diseases.

In addition, several serious acute diabetic complications such as diabetic ketoacidosis and lactic acidosis can occur, often with lethal consequences, especially in the elderly [see e.g., Textbook of Diabetes (2nd Edition) J. Pickup and G. Williams, Eds. (1997) Blackwell Science, Oxford].

Most patients can be clinically classified as having either insulin-dependent diabetes mellitus (IDDM or Type-I diabetes) or non-insulin-dependent diabetes mellitus (NIDDM or Type-II diabetes). In the United States about 90% of diabetic patients have Type-II diabetes and most of the remainder suffer from Type-I diabetes.

There is evidence that Type-I diabetes is an autoimmune disease of the pancreatic β-cells leading to their continuous destruction [Srikanta, S. et al. (1983) Ann. Intern. Med. 99,320-326]. In Type-II diabetes there is no significant loss of β-cells from pancreatic islets, although the β-cells retain their ability to synthesize and secrete insulin and their ability to respond to a glucose challenge is diminished, especially through the first phase of insulin secretion [Cerasi, E. & Luft, R. (1963) Lancet ii: 1359-1361; Cerasi, E. & Luft, R. (1967) Acta ENDOCR. (KBH) 55, 278-304 ; Cerasi, E. & Luft, R. (1967) Acta Endocr. (Kbh.) 55,330-45; Cerasi, E. & Luft. R. (1967) Diabetes 16,615-627; Genuth, S. (1973) Ann. Intern. Med. 79,812-822; Leahy, J. L. et al. (1987) J CLIN. INVEST. 77,908-915; Cerasi, E. In F. M. Ashcroft & S. J. H. Ashcroft, Eds. Insulin: Molecular Biology to Pathology. Oxford University Press (1992), pp. 347-92; Nesher, R., et al. (1999) Diabetes 48,731-737 ; Cerasi, E., et al. (2001) Diabetes 50 (Suppl. 1): S1-S3].

The search for novel compounds and drugs that can reduce blood glucose levels in diabetic patients is a major topic in diabetes research. Hyperglycemia is the main cause of diabetic complications, such as cardiovascular disease, nephropathy, neuropathy and retinopathy. Most available drugs act primarily on the insulin-secreting cells (i.e., the β-cells in the pancreas) to increase or potentiate insulin release. In many cases these drugs are ineffective due to various reasons, including deterioration of the β-cells and peripheral insulin resistance. It is therefore clear that drugs that increase glucose transport and utilization in peripheral tissues in a non-insulin-dependent manner may be beneficial to treat hyperglycemic diabetic patients.

A major pathophysiological phenomenon in diabetes is the existence of insulin resistance and decreased peripheral glucose utilization [DeFronzo, R. et al (1982) Diabetologia, 313-319]. Three series of observations in diabetic patients indicate that this insulin resistance may itself be associated with the prevailing hyperglycemia. First, most of the defect is in terms of reduction of the maximal velocity of glucose utilization rather than change in the sensitivity to insulin, thus being different from the common insulin resistance like obesity [Olefsky, J. M. et al (1981) Am. J. Med 70,151-168]. Second, the insulin resistance is partially corrected if tested at the patient's habitual hyperglycemic glucose level rather than during acutely induced euglycemia [Revers, R. et al. (1984) R Clin. Invest. 73,664-672, Nesher, R., et al. (1984) Eur. J Clin. Invest. 17,266-274]. Third, induction of normoglycemia by various means corrects the decreased glucose utilization within several weeks [Nesher et al (1984) ibid; Andres, W. J. et al. (1984) Diabetes 33,634-642; Garvey, W. T. et al. (1985) Diabetes 34, 224-234; Sasson, S. et al. (1986) J: Biol. Chem. 261,16827-16833 ; Sasson, S. et al. (1987) Diabetes 36,1041-1046; Savage, P. J. et al. (1979) J: Clin. Endocrinol. Metab. 48,999-1007; Wertheimer, E. et al. (1990) J Cell. Physiol. 143,330-336]. This suggests that peripheral tissues make use of the glucose mass effect to compensate for the reduced Vmax of uptake. Thus, this insulin resistance, at least partially, seems to be a phenomenon secondary to hyperglycemia. The inventors have recently shown that adaptive down-regulation of glucose transport occurs during hyperglycemia. [Sasson, S. et al. (1986) *J. Biol. Chem.* 261, 16827-16833; Sasson, S. et al. (1987) *Diabetes* 36, 1041-1046; Wertheimer, E. et al. (1990) *J. Cell. Physiol.* 143, 330-336; Cerasi, E. et al. (1989) In Frontiers of Diabetes Research: Current Trends in Non-Insulin-Dependent Diabetes Mellitus (Alberti, K. and Mazze, R., eds.), pp. 309-320, Elsevier Science Publishers, New York; Cerasi, E and Sasson, S. (1992) *Journees de Diabetologie,* 23-36; Sasson, S. et al (1990) in Frontiers in Diabetes Research II. Lessons from animal diabetes III (ed. E. Shafrir) pp. 355-359, Smith-Gordon, New York; Sasson, S. et al. (1997) *Diabetologia* 40, 40:30-398; Wertheimer, E. et al. (1991) *Proc. Natl. Acad. Sci. (USA)* 88, 2525-2529].

The hexose transport system in mammalian cells is subject to complex regulation. The main glucose consumers of the organism, muscle and fat cells, contain two types of glucose transporters: GLUT 1, which is mainly in charge of transporting glucose into the cell under basal conditions, and GLUT 4 which is markedly responsive to insulin and stands for the stimulation of glucose uptake by insulin. The inventors have previously shown that the uptake and utilization of hexose in cultured rat myocytes and myotubes are dependent on the D-glucose concentration to which the cells are pre-exposed [Garvey et al (1985) op cit.; Sasson et al (1987), Wertheimer et al (1990) op cit; Cerasi, E. et al. (1989) op cit.; Cerasi, E and Sasson, S. (1992) op cit.; Wertheimer, E. et al. (1991) op cit.]. Similar effects of glucose withdrawal and refeeding have been reported in cultured L6 [Walker, P. S. et al. (1990) *J. Biol. Chem.* 265, 1516-1523] and BC3H1 skeletal muscle cells [el-Kabbi, I. M. et al. *Biochem. J.* 30, 35-40]. In L8 skeletal muscle cells exposed to increasing glucose concentrations, the maximal velocity of hexose transport (Vmax)

was reduced in a concentration-dependent manner, while affinity (Km) was unaffected [Sasson, S. and Cerasi, E. (1986) op cit.].

Cytochalasin B binding and Western blotting of enriched plasma- and microsomal-membrane fractions revealed that high glucose concentrations modulated the subcellular distribution of GLUT-1, reducing their number at the plasma membrane of the cell [Sasson, et al (1997); Greco-Perotto, R. et al. (1992) *Biochem. J.* 286, 157-163]. In addition, glucose reduced time-dependently the GLUT-1 mRNA level in L8 myocytes [Wertheimer et al (1991) op cit.]. Similar autoregulatory effects of glucose were found in a variety of cells (for review, see [Klip, A. et al. (1994) *FASEB J.* 8, 43-53]). It has been proposed that the downregulation of glucose transport and utilization via this substrate autoregulatory mechanism may play an important role in glucose homeostasis [Cerasi et al (1989), 2 Mathoo et al. (1999) *Diabetes* 48:1281-1288; Rossetti, L. et al. (1990) *Diabetes Care* 13, 610-630; Yki-Jarvinen, H. (1990) *Diabetologia* 33, 579-585]. The inventors have shown [Sasson et al (1997) op cit.] that the accumulation of hexose-6-phosphate in the cells may be related to this mechanism, serving as intermediary between the extracellular glucose concentration and the cellular mechanism that effectuates GLUT translocation.

The inventors have recently observed that high glucose levels affect similarly the cellular distribution of GLUT-4. C2 and L6 skeletal muscle cells and 3T3-L1 adipocytes express both GLUT-1 and GLUT-4; when exposed to a high glucose concentration (20 mM) the density of both transporters in the plasma membrane of the cells is decreased. These findings were obtained by a cell-surface biotinylation technique followed by purification of the biotinylated proteins and Western blotting with specific antisera. Moreover, similar results were confirmed by laser confocal microscopy of the cells.

U.S. Pat. No. 5,468,734 discloses methods and compositions remedying a disease attendant on hyperglycemia, which comprise administering at least one monosaccharide selected from L-arabinose, L-fucose, 2-deoxy-D-galactose, D-xylose, L-xylose, D-ribose, D-ribulose, D-lyxose and D-xylulose. The Specification discloses that it has been found that some pentoses and hexoses are effective in depressing the rise in blood sugar after carbohydrate loading.

U.S. Pat. No. 6,329,344 discloses substituted pentose and hexose monosaccharide derivatives, which exhibit anti-cell adhesion and anti-inflammatory activities. U.S. Pat. No. 5,432,163 discloses derivatives of pentose monosaccharides, which exhibit anti-proliferative and anti-inflammatory activity, as well as methods of treating inflammatory and/or autoimmune disorders employing these compounds. WO01/51058 discloses cyclic ethers of monosaccharides, e.g. 1,5-anhydro-D-fructose (1,5AnFru) or derivatives of 1,5AnFru, and their use in the modulation of glucose metabolism in mammals, in particular in the increase of glucose tolerance.

Given the high incidence of diabetes and hyperglycemia in society, and the serious and sometimes life-threatening complications associated with abnormally high blood glucose levels, there is an urgent need in the medical art to develop new therapeutic approaches to the treatment and/or prevention or hyperglycemia and the complications arising therefrom and to the control and treatment of diabetes.

SUMMARY OF THE INVENTION

The present invention relates to pentoses and pentose derivatives that are effective at increasing glucose transport in a non-insulin dependent manner, and to uses thereof for a) treating and/or preventing hyperglycemia; b) treating and/or preventing the complications of hyperglycemia; c) treating diabetes; d) increasing the rate of cellular glucose transport; e) increasing the rate of cellular glucose uptake; f) improving the ability of a subject to metabolize glucose; g) treating daily blood glucose fluctuations; h) reducing blood sugar levels; and i) reducing the dosage of anti-diabetic medication needed for treatment of diabetes. The present invention further provides novel pentose derivatives having beneficial properties in terms of pharmacokinetics, to pharmaceutical compositions comprising these novel compounds and uses thereof.

In one embodiment, the present invention provides novel pentose derivatives that are effective at increasing glucose transport in a non-insulin dependent manner which are represented by at least one of the structures of formulae I-III:

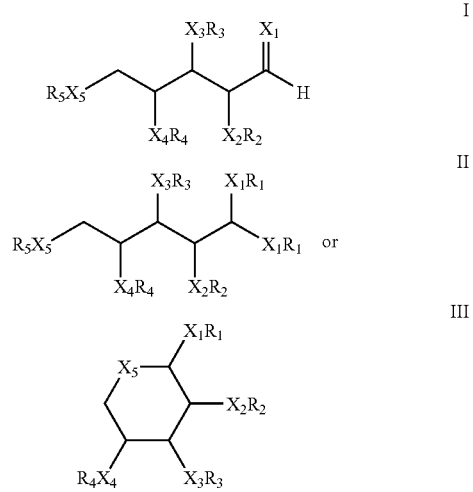

wherein
$X_1$ and $X_3$ are O or S;
$R_1$ and $R_3$ are independently of each other hydrogen, a $C_1$-$C_6$ alkyl, an O or S protecting group, or an amino acid containing a thiol or hydroxyl group in its side-chain;
$X_2$, $X_4$ and $X_5$ are independently of each other O, S, or NH;
$R_2$, $R_4$ and $R_5$ are independently of each other hydrogen or an O, S or N protecting group,
provided that when $X_1$-$X_5$ are oxygen and $R_2$, $R_4$ and $R_5$ are hydrogen,
at least one of $R_1$ and $R_3$ is other than hydrogen or methyl;
or a pharmaceutically acceptable salt, hydrate or derivative thereof.

In one embodiment, the pentose derivative is a xylose, ribose, arabinose or lyxose derivative. In one preferred embodiment, the pentose derivative is a xylose derivative. In another preferred embodiment, the pentose derivative is a D-xylose derivative. In yet another preferred embodiment, the pentose derivative is represented by the structure of formula I, i.e. an aldehyde or thioaldehyde. In another preferred embodiment, the pentose derivative is represented by the structure of formula II, i.e. an acetal or thioacetal. In another preferred embodiment, the pentose derivative is represented by the structure of formula m, i.e. a ring pyranoside or thiopyranoside.

In one embodiment, $X_1$ in any of the formulae I-III is O. In another embodiment, $X_1$ in any of the formulae I-III is S. In another embodiment, $R_1$ in any of the formulae I-III is methyl. In another embodiment, $R_1$ in any of the formulae I-III is ethyl. In another embodiment, $R_1$ in any of the formulae I-III is propyl. In another embodiment, $R_1$ in any of the formulae I-III is isopropyl. In one embodiment, $X_3$ in any of the formulae I-III is O. In another embodiment, $X_3$ in any of the formulae I-III is S. In another embodiment, $R_3$ in any of the formulae I-III is methyl. In another embodiment, $R_3$ in any of the formulae I-III is ethyl. In another embodiment, $R_3$ in any of the formulae I-III is propyl. In another embodiment, $R_3$ in any of the formulae I-III is isopropyl. In another embodiment, $X_1$ is S and $R_1$ is methyl. In another embodiment, $X_1$ is S and $R_1$ is ethyl.

A suitable protecting group for the compounds of the present invention is a benzylidene (—CH-phenyl) moiety. A benzylidene acetal is formed from a reaction of hydroxyls with benzaldehyde. A benzylidene thioacetal is formed from a reaction of thiols with benzaldehyde. Other suitable protecting groups include hexalidene, pentalidene and octalidene, formed from a reaction with hexa-, penta- or octaldehyde. An acetonide or thioacetonide moiety formed by reaction with acetone is also contemplated by the present invention.

In one embodiment of Formulas I-III, any one or more of a) $R_1$ together with $R_2$; b) $R_1$ together with $R_3$; c) $R_2$ together with $R_3$; d) $R_2$ together with $R_4$; e) $R_3$ together with $R_4$; f) $R_3$ together with $R_5$; or g) $R_4$ together with $R_5$, independently of each other represent a $CR_6R_7$ group wherein $R_6$ and $R_7$ are independently of each other a hydrogen, a linear or branched-chain alkyl or a phenyl.

A preferred protecting group for the present invention is a benzylidene moiety, formed by reaction of the hydroxyls, thiols or amines with benzaldehyde. It is understood that when one of $R_6$ and $R_7$ represent a hydrogen and the other represents a benzyl, the $CR_6R_7$ group is a benzylidene group.

In one embodiment, any one or more of a) $R_1$ together with $R_2$; b) $R_1$ together with $R_3$; c) $R_2$ together with $R_3$; d) $R_2$ together with $R_4$; e) $R_3$ together with $R_4$; f) $R_3$ together with $R_5$; or g) $R_4$ together with $R_5$, independently of each other represent a $CR_6R_7$ group wherein $R_6$ and $R_7$ are independently of each other a hydrogen, an alkyl or phenyl. In one preferred embodiment, $R_2$ together with $R_4$ represent a CH-phenyl group. In another preferred embodiment, $R_3$ together with $R_5$ represent a CH-phenyl group. In another preferred embodiment, both $R_2$ together with $R_4$ and $R_3$ together with $R_5$ each represent a CH-phenyl group. In another preferred embodiment, $R_1$ together with $R_2$ represent a CH-phenyl group.

In another embodiment, the present invention provides a methoxy-polyethyleneglycol (PEG) derivative of any one or more of the pentoses provided herein.

In another embodiment, the present invention provides a pentose derivative represented by at least one of the structures of formulae IV-V:

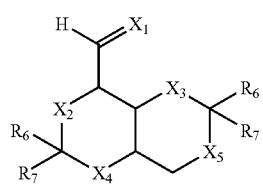

IV

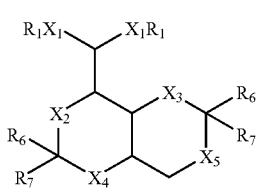

V wherein $X_1$-$X_5$, $R_1$, $R_6$ and $R_7$ are as defined above.

In yet another embodiment, the present invention provides a pentose derivative represented by at least one of the structures of formulae VI-VII:

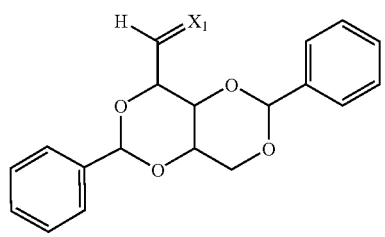

VI

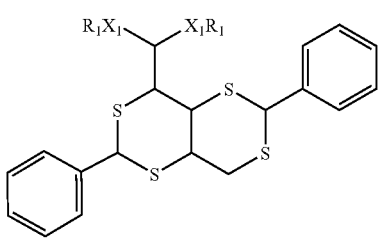

VII wherein $X_1$ and $R_1$ are as defined above.

As contemplated herein, specific non-limiting examples of the pentose derivatives that are included within the scope of the present invention are: di-4-O-(1-O-methyl-α-xylopyranoside)-phosphoryl-O-methyl-PEG; 2,4:3,5-di-O-benzylidene-D-xylose-dimethylacetal; 2,4:3,5-di-O-benzylidene-D-xylose-diethyl-dithioacetal; 3-O-ethyl-2,4-O-benzylidene-D-xylose-diethyl-dithioacetal; propyl-thio-β-xylopyranoside; ethyl-thio-β-xylopyranoside; lauryl-thio-β-xylopyranoside; D-xylose-di-N-acetylcysteine-dithioacetal; D-xylose-di-cysteine-dithioacetal; D-xylose-diethyl-dithioacetal; D-xylose-dipropyl-dithioacetal; 1,3-O-dimethylxylopyranoside; 2,4-benzylidene-D-xylose-diethyl-dithioacetal; 3-O-methyl-2,4-O-benzylidene-D-xylose-diethyl-dithioacetal, 3-O-propyl-2,4-O-benzylidene-D-xylose-diethyl-dithioacetal, 3-O-ethyl-5-O-benzoyl-D-xylose-diethyl-dithioacetal, 3-O-propyl-1,2-benzylidene-D-xylose and 3-O-propyl-2,4-benzylidene-D-xylose. It is understood that these examples are provided in order to set forth different embodiments of the present invention, and should not be construed in any way as limiting the broad scope of the pentose derivatives provided by the present invention.

In another embodiment, the present invention provides a composition comprising the pentose derivative of any of formulae I-VII as described hereinabove, or a pharmaceutically acceptable salt or hydrate thereof In another embodiment, the present invention provides a pharmaceutical composition comprising the pentose derivative of any of formulae I-VII as described hereinabove, or a pharmaceutically acceptable salt or hydrate thereof, and a pharmaceutically acceptable carrier.

The pentose derivatives provided herein are effective at increasing glucose transport in a non-insulin dependent manner and to uses thereof for a) treating and/or preventing hyperglycemia; b) treating and/or preventing the complications of hyperglycemia; c) treating diabetes; d) increasing the rate of cellular glucose transport; e) increasing the rate of cellular glucose uptake; f) improving the ability of a subject to metabolize glucose; g) treating daily blood glucose fluctuations; h) reducing blood sugar levels; and i) reducing the dosage of anti-diabetic medication needed for treatment of diabetes.

Thus, in one embodiment, the present invention provides a method of preventing or treating hyperglycemia in a subject, comprising the step of administering to the subject a pentose derivative of the present invention, in an amount effective to lower blood glucose levels in the subject, thereby preventing or treating hyperglycemia in the subject.

In another embodiment, the present invention provides a method of preventing or treating complications of hyperglycemia in a hyperglycemic subject, the method comprising the step of administering to the subject a pentose derivative of the present invention, in an amount effective to lower blood glucose levels in the subject, thereby preventing or treating the complication of hyperglycemia in the subject. Non-limiting examples of complications of hyperglycemia are cardio-vascular disease, diabetic neuropathy, nephropathy, retinopathy, glaucoma, cataract, diabetic ketoacidosis, lactic acidosis, and insulin resistance.

Furthermore, in another embodiment, the present invention provides a method of treating diabetes in a subject, comprising the step of administering to the subject a pentose derivative of the present invention, in an amount effective to lower blood glucose levels in the subject, thereby treating diabetes in the subject. In one embodiment, the diabetes is diabetes mellitus. In another embodiment, the diabetes is insulin-dependent diabetes mellitus (Type-I diabetes). In yet another embodiment, the diabetes is non-insulin-dependent diabetes mellitus (Type-II diabetes).

Furthermore, in another embodiment, the present invention provides a method of increasing the rate of cellular glucose transport in a subject, comprising the step of administering to the subject a pentose derivative of the present invention, in an amount effective to increase the rate of cellular glucose transport in the subject.

Furthermore, in another embodiment, the present invention provides a method of increasing the rate of cellular glucose uptake in a subject, comprising the step of administering to the subject a pentose derivative of the present invention, in an amount effective to increase the rate of cellular glucose uptake in the subject.

Furthermore, in another embodiment, the present invention provides a method for improving the ability of a subject to metabolize glucose, the method comprising administering to the subject a pentose derivative of the present invention, in an amount effective to improve the ability of a subject to metabolize glucose.

Furthermore, in another embodiment, the present invention provides a method for treating daily blood glucose fluctuations in a subject susceptible to daily blood glucose fluctuations, the method comprising administering to the subject a pentose derivative of the present invention, in an amount effective to treat daily blood glucose fluctuations in a subject susceptible to daily blood glucose fluctuations.

Furthermore, in another embodiment, the present invention provides a method for reducing blood sugar levels in a subject susceptible to abnormal fluctuations in blood sugar levels, the method comprising administering to the subject a pentose derivative of the present invention, in an amount effective to reduce blood sugar levels in a subject susceptible to abnormal fluctuations in blood sugar levels.

Furthermore, in another embodiment, the present invention provides a method for reducing the dosage of anti-diabetic medication needed for treatment of a diabetic subject, the method comprising administering to the subject a pentose derivative of the present invention, in an amount effective to reduce the dosage of anti-diabetic medication needed for treatment of a diabetic subject.

In one embodiment, the subject is a mammalian subject. In another embodiment, the subject is a human subject. In another embodiment, the subject is a non-human mammalian subject.

In one embodiment, the pentose of the present invention is administered as a pharmaceutical preparation comprising the pentose derivative, and a pharmaceutically acceptable carrier.

Furthermore, in one embodiment, the present invention provides a method of increasing the rate of glucose transport in a cell, comprising the step of contacting the cell with a pentose derivative of the present invention, in an amount effective to increase the rate of glucose transport in the cell. In another embodiment, the present invention provides a method of increasing the rate of glucose uptake by a cell, comprising the step of contacting the cell with a pentose derivative of the present invention, in an amount effective to increase the rate of glucose transport in the cell. In one embodiment, the cell is a mammalian cell. In another embodiment, the cell is a human cell.

As demonstrated herein, the unexpected results demonstrate that pentose derivatives, particularly D-xylose derivatives represented by the structure of formulas I-III, are effective at increasing the rate of glucose transport and glucose uptake in insulin-responsive cells. Consequently, these pentoses may be utilized as therapeutic agents for a) treating and/or preventing hyperglycemia; b) treating and/or preventing a complication or hyperglycemia; c) treating diabetes; d) increasing the rate of cellular glucose transport; e) increasing the rate of cellular glucose uptake; f) improving the ability of a subject to metabolize glucose; g) treating daily blood glucose fluctuations; h) reducing blood sugar levels; and/or i) reducing the dosage of anti-diabetic medication needed for treatment of diabetes.

BRIEF DESCRIPTION OF THE DRAWINGS

The present invention will be understood and appreciated more fully from the following detailed description taken in conjunction with the appended drawings.

Figure 4A:
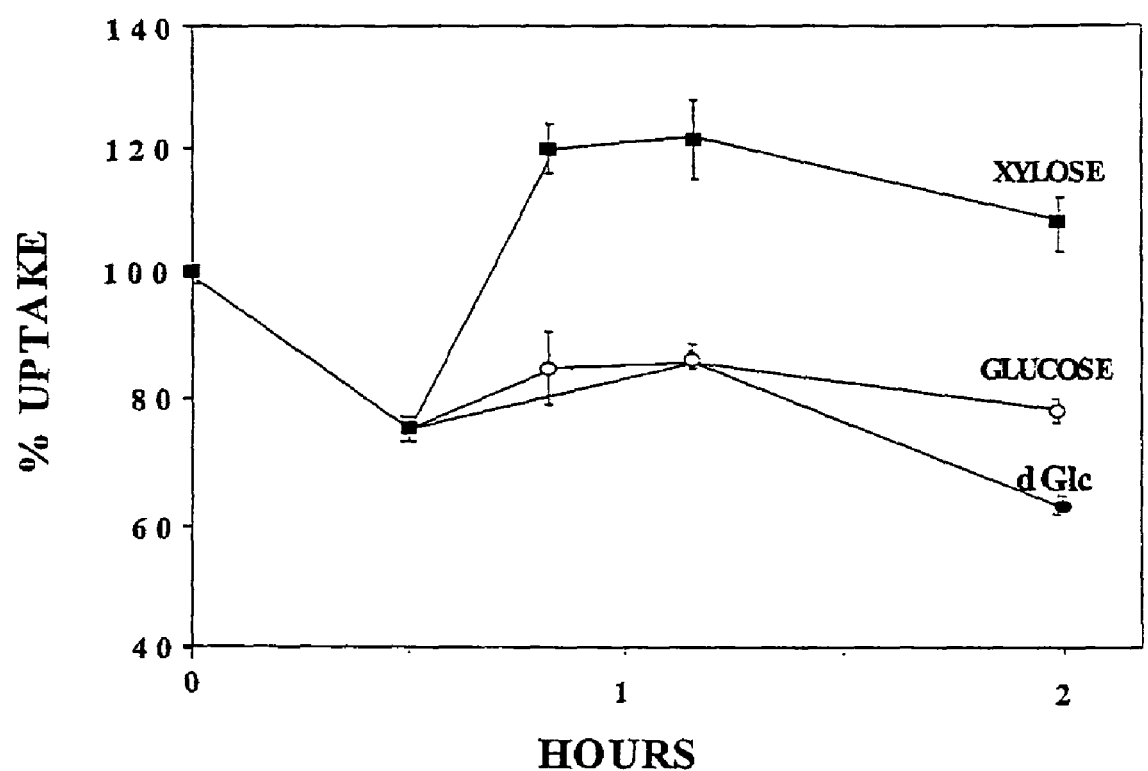
Figure 4B:
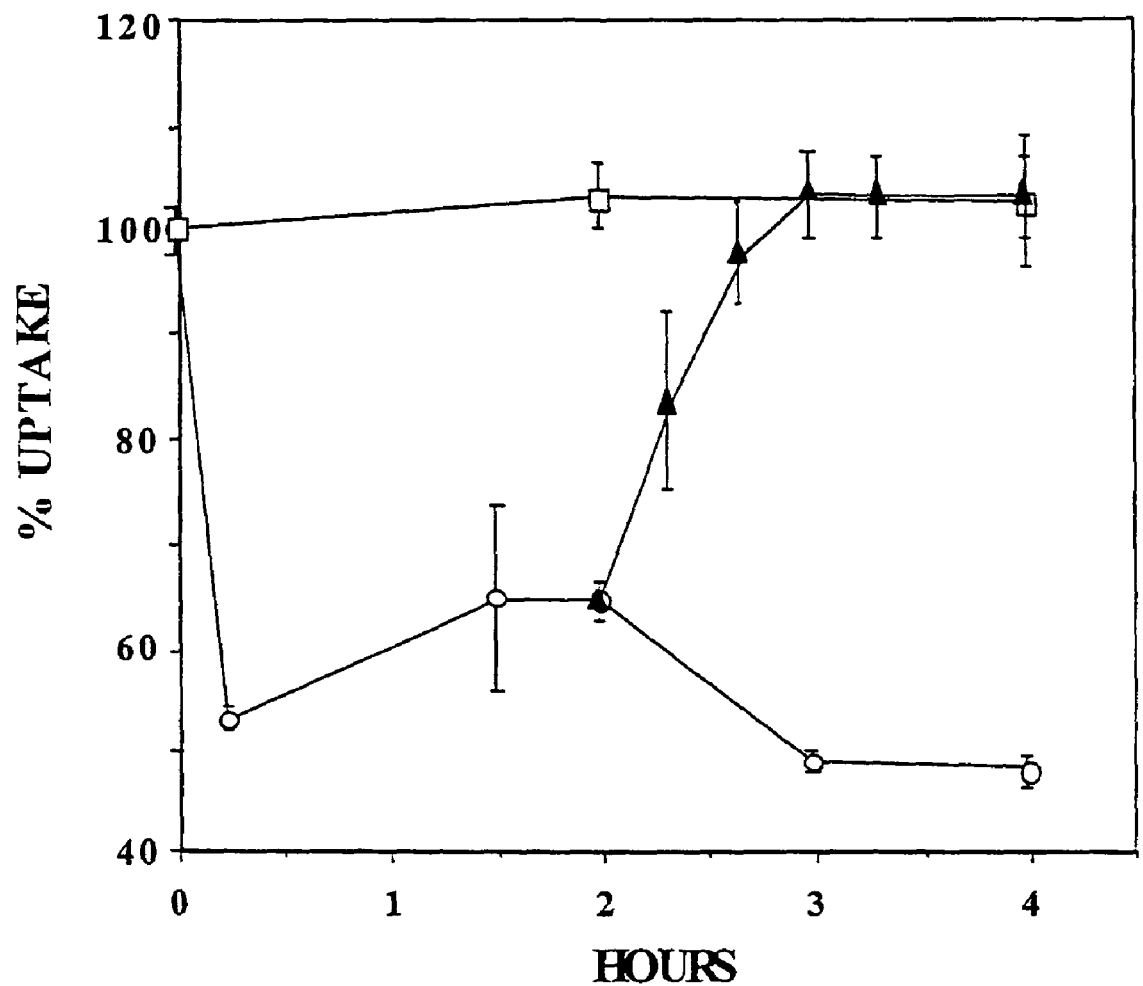

FIG. 4A:

FIG. 4B: Effect of D-xylose on rate of hexose transport following treatment with dGlc. A) C2 myotubes preconditioned with 2 mM glucose received fresh medium containing 2 mM dGlc. A portion of the cells were washed after 30 min and received 20 mM D-xylose or 2 mM D-glucose or glucose. dGlc uptake assay was performed at the indicated times. 100%=1.05±0.03 nmol dGlc/mg protein/min. B) L8 myocytes preconditioned with 2 mM glucose were washed and incubated with 2 mM glucose (open rectangle) or 2 mM dGlc (open circle). A portion of the cells were washed again after 2 hr and incubated with 20 mM xylose (black triangle). At the indicated times the cells were subjected to the dGlc uptake assay. 100%=198.6±4.4 pmol/dGlc/million cells/min. Mean±SEM (n=3).

Figure 5:
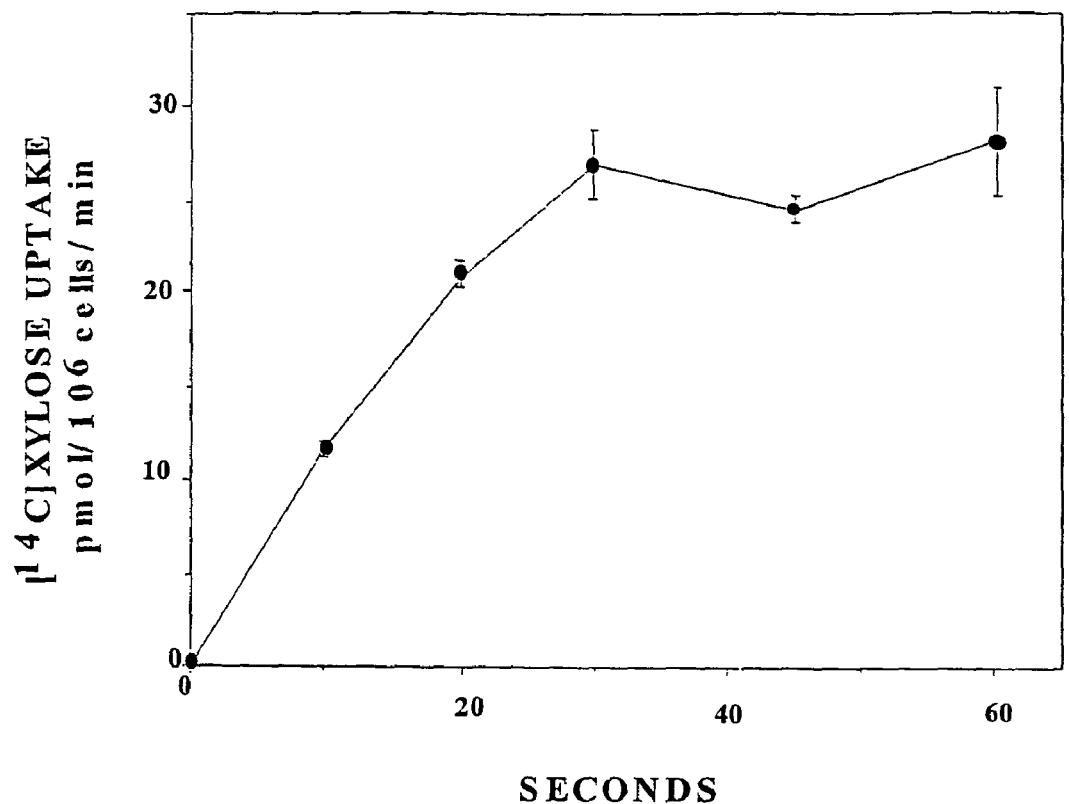

FIG. 5: [$^{14}$C]D-xylose uptake by cells. C2 myotubes conditioned with 2 mM glucose were washed and subjected to [$^{14}$C]xylose uptake assay (0.1 mM xylose). The assay was similar to the dGlc uptake assay. Mean±SEM (n=3).

Figure 6:
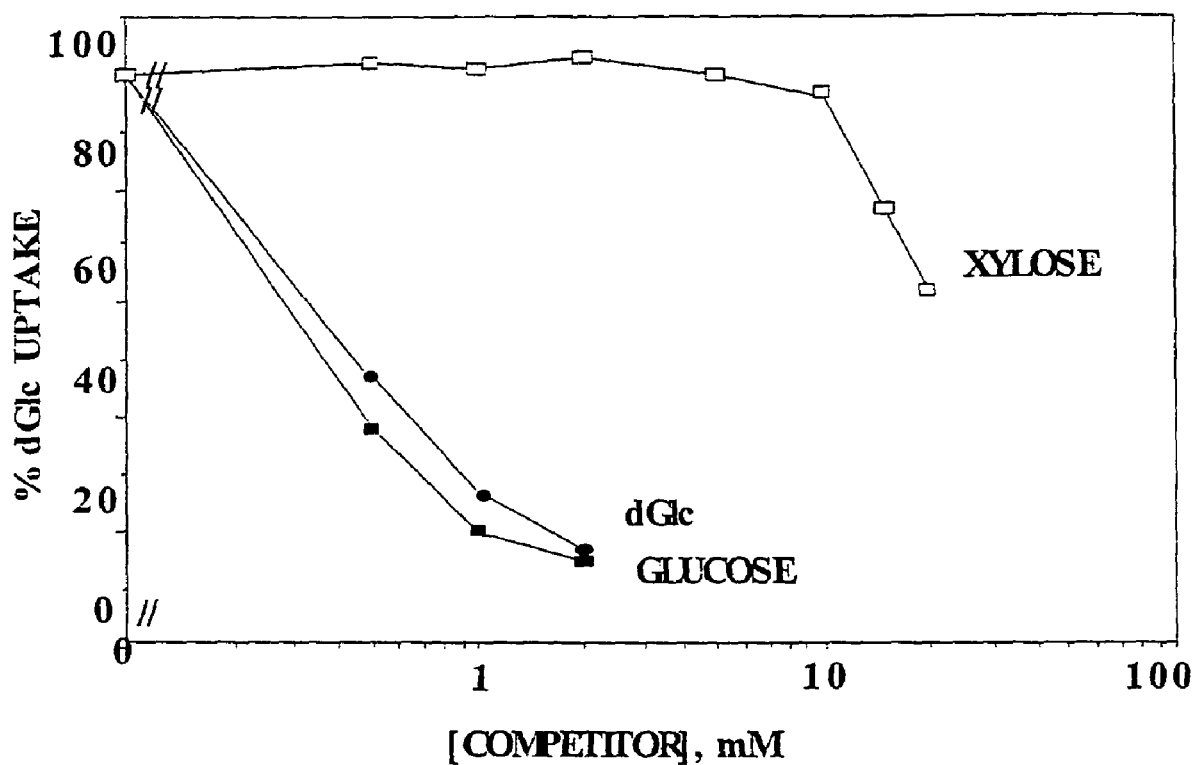

FIG. 6: Lack of affinity of D-xylose for the glucose transporters. C2 myotubes preconditioned with 20 mM glucose were subjected to [$^{3}$H]dGlc uptake assay (0.1 mM dGlc) with increasing concentrations of unlabeled dGlc, glucose or xylose. The unlabeled carbohydrates were added to the [$^{3}$H] dGlc solution in the uptake assay.

Figure 7:
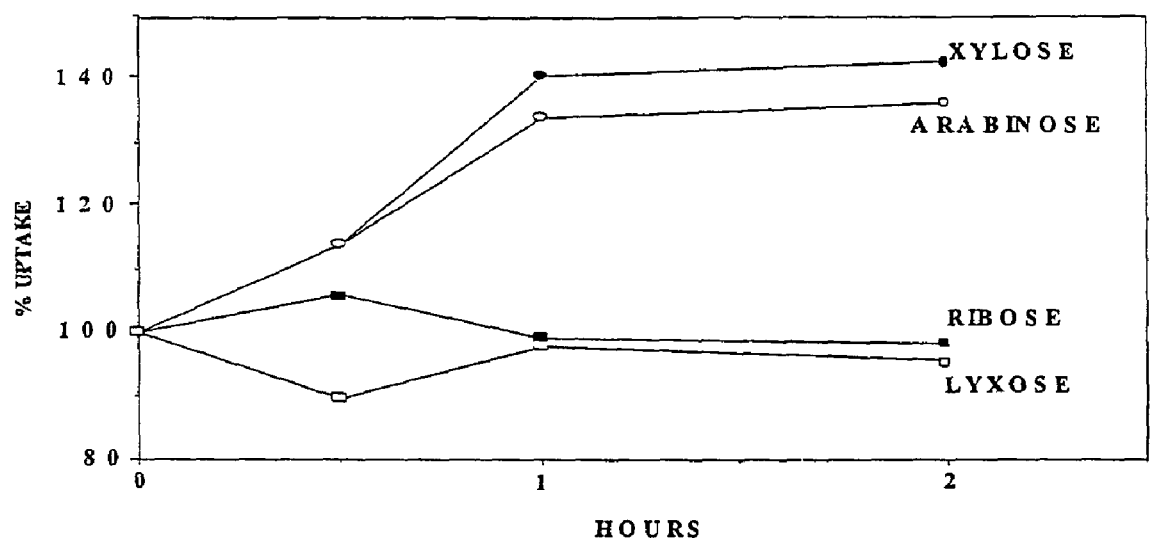

FIG. 7: Effect of different pentoses on the rate of hexose transport. C2 myotubes preconditioned with 20 mM glucose were washed and incubated with 20 mM xylose (black circle), arabinose (open circle), lyxose (open rectangle) or ribose (black rectangle). Cells were subjected to the dGlc uptake assay at the indicated times. 100%=1.64±0.06 pmol/mg protein/min. Mean±SEM (n=3).

Figure 8:
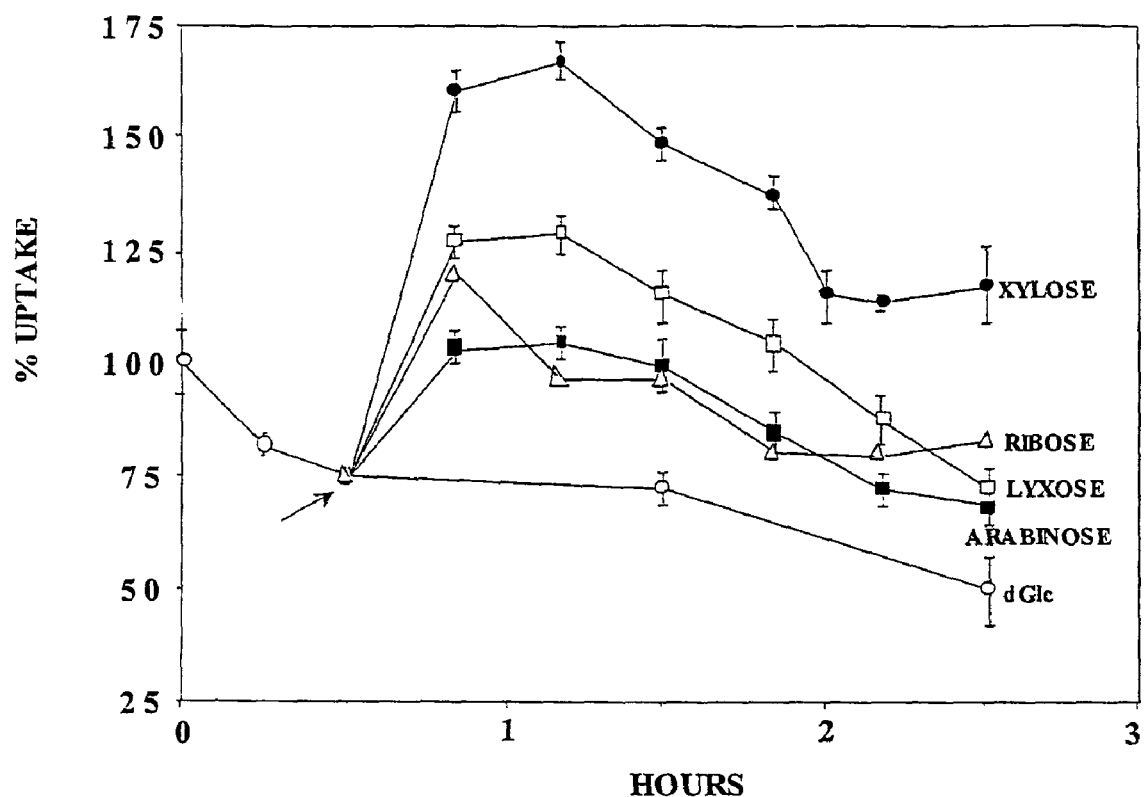

FIG. 8: Reversal of 2-deoxy-D-glucose-induced downregulation of the hexose transport system. L8 myocytes were preconditioned with 2 mM glucose, washed and incubated with 2 mM dGlc (open circle). After 30 min a portion of the cells were washed again and were incubated with 20 mM xylose (black circle), ribose (open triangle), arabinose (black rectangle) or lyxose (open rectangle). Cells were subjected to the dGlc uptake assay at the indicated times. 100%=122.8±0.01 pmol dGlc/$10^6$ cells/min. Mean±SEM (n=3).

Figure 9:
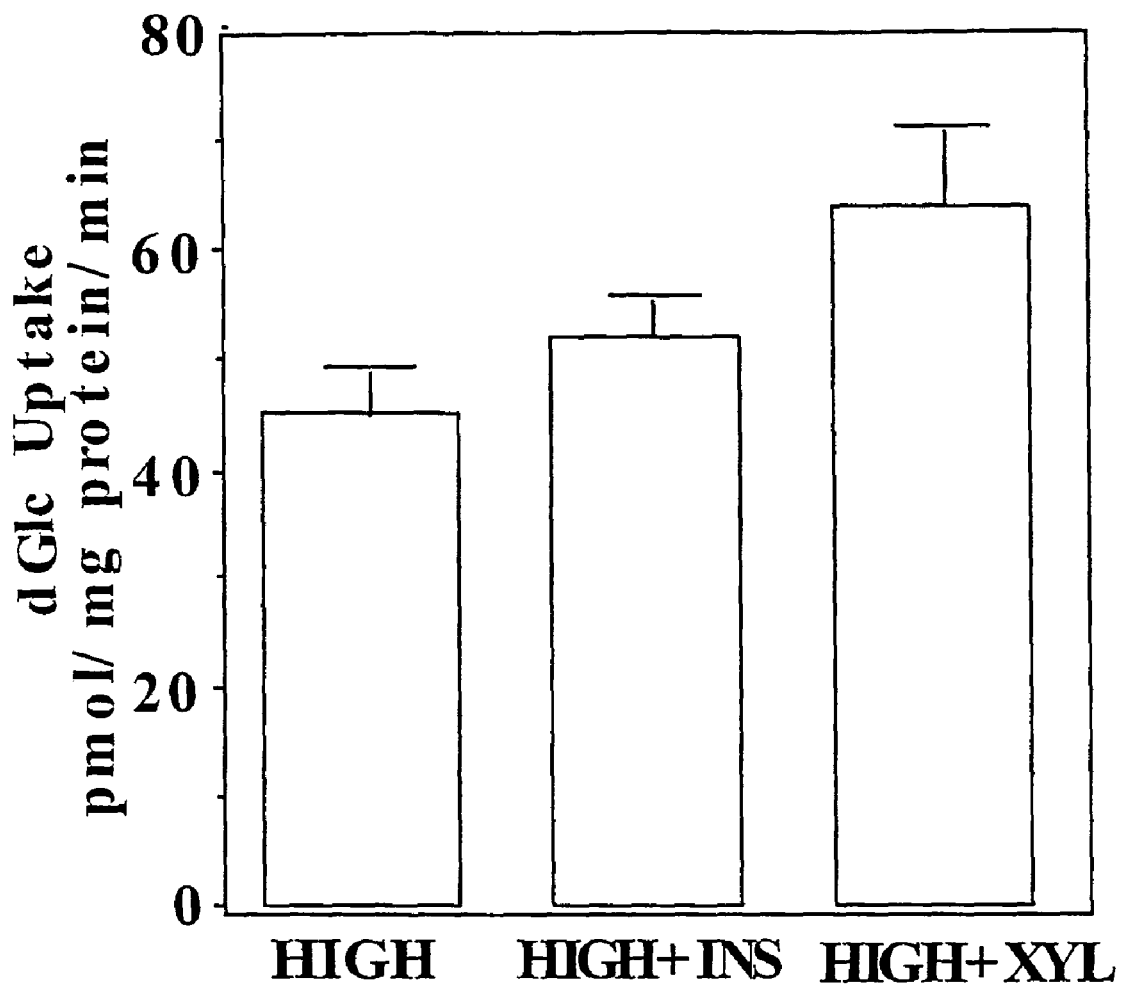

FIG. 9: Effect of D-xylose on dGlc uptake in soleus muscles. Soleus muscles were isolated from Sabra male albino rats and incubated for 3 hr with 20 mM glucose in the absence or the presence of 20 mM xylose. The muscles were washed and subjected to dGlc uptake assay without or with insulin (500 nM). Mean±SEM (n=3).

Figure 10:
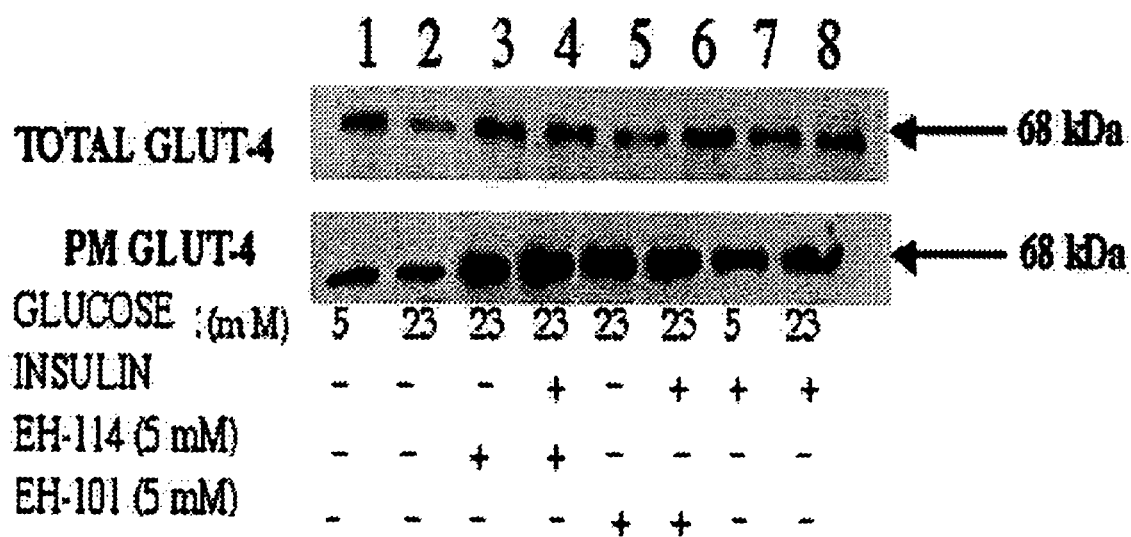

FIG. 10: Western blot depicting effect of 3-O-propyl-D-xylose (EH-114), and 1,3-O-dimethylxylopyranoside (EH-101) on the total cell content and plasma membrane abundance of GLUT-4 in the absence or presence of insulin. L6 myotubes were maintained for 48 hr at 23 mM Glucose. The cells were than washed and received fresh medium containing the indicated additions and incubated for additional 20 hr. Insulin was added during the last 30 min of incubation before the dGlc uptake assay.

Figure 11A:
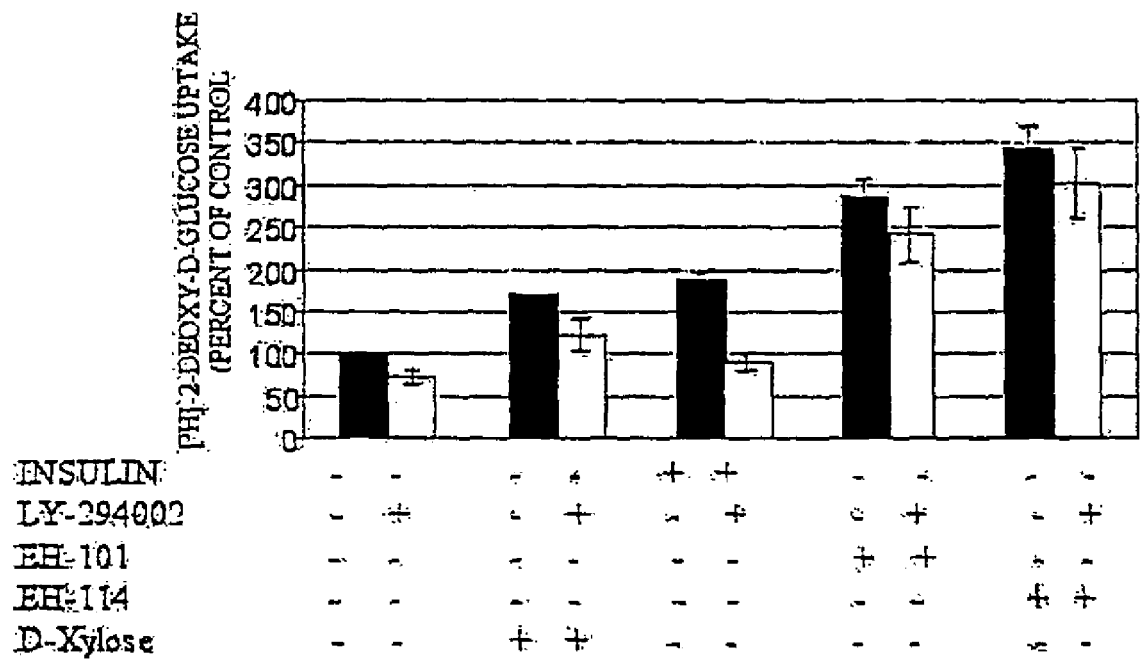

FIG. 11A: Effect of LY-249002, a PI3-kinase inhibitor, on insulin, D-xylose, EH-101 and EH-114-mediated glucose uptake. L6 myotubes were treated as described in the legend to FIG. 10. The glucose concentration in the culture medium was 23.0 mM. The concentration of LY-294002 was 60 μM. At the end of incubation the cells were taken for the standard dGlc uptake assay. Mean±SEM, n=3.

Figure 11B:
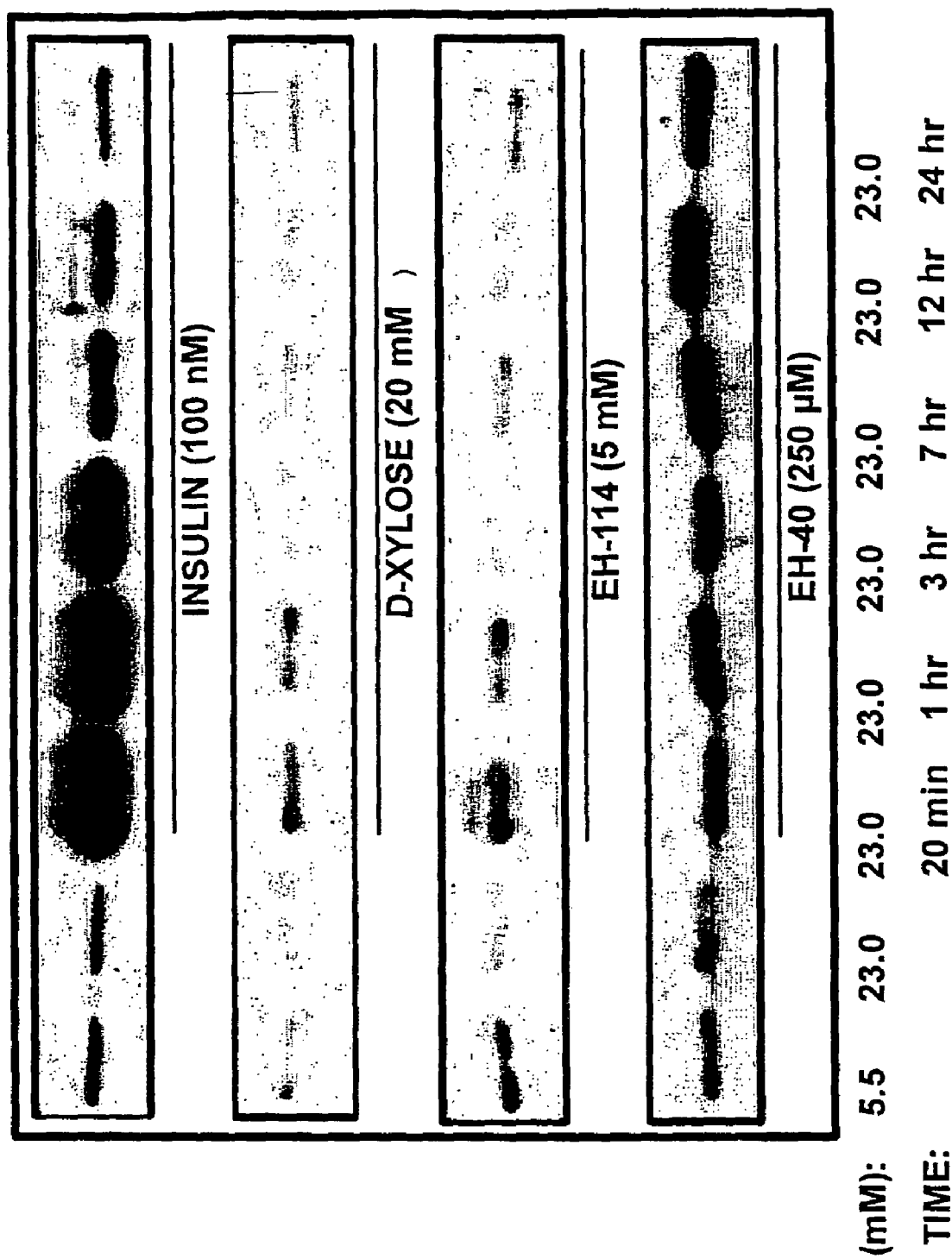

FIG. 11B: Effects of insulin D-xylose and xylose derivatives on PKB phosphorylation. L6 myotubes were maintained at 5.5 mM or 23.0 mM glucose. The latter were treated with 100 nM insulin, 20 mM xylose, 5 mM EH-114 or 250 μM EH-40 up to 24 hrs. At the indicated times treated myotubes were collected, homogenized and lysed and the soluble protein fraction was isolated. The control myotubes were collected at the end of the 24 hr incubation period. Equal amounts of proteins of the various treated myotubes were separated on SDS-PAGE and immunoblotted with a specific antibody against phospho-Axt1/PKBα (Ser473).

Figure 12:
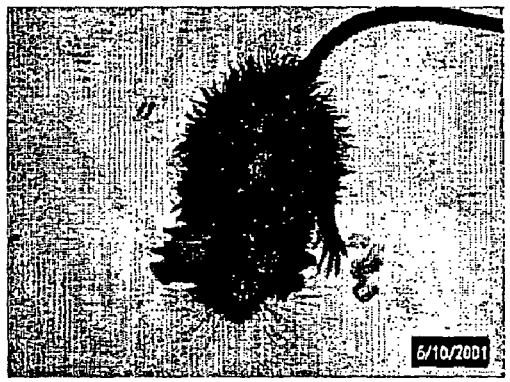
Figure 12:

FIG. 12: Anti-hyperglycemic activity of EH-36 in streptozotocin-diabetic mice. Mice were treated with EH-36 or the vehicle alone (sesame oil, bold lines), and their blood glucose levels determined at the indicated time intervals. Male C57/ black mice were made hyperglycemic by 5 repeated daily injections of streptozotocin (i.p. 50 mg/Kg body weight). EH-36 was dissolved in sesame oil (4 mg/ml) and injected s.c (400 μg) twice a day.

Figure 13:
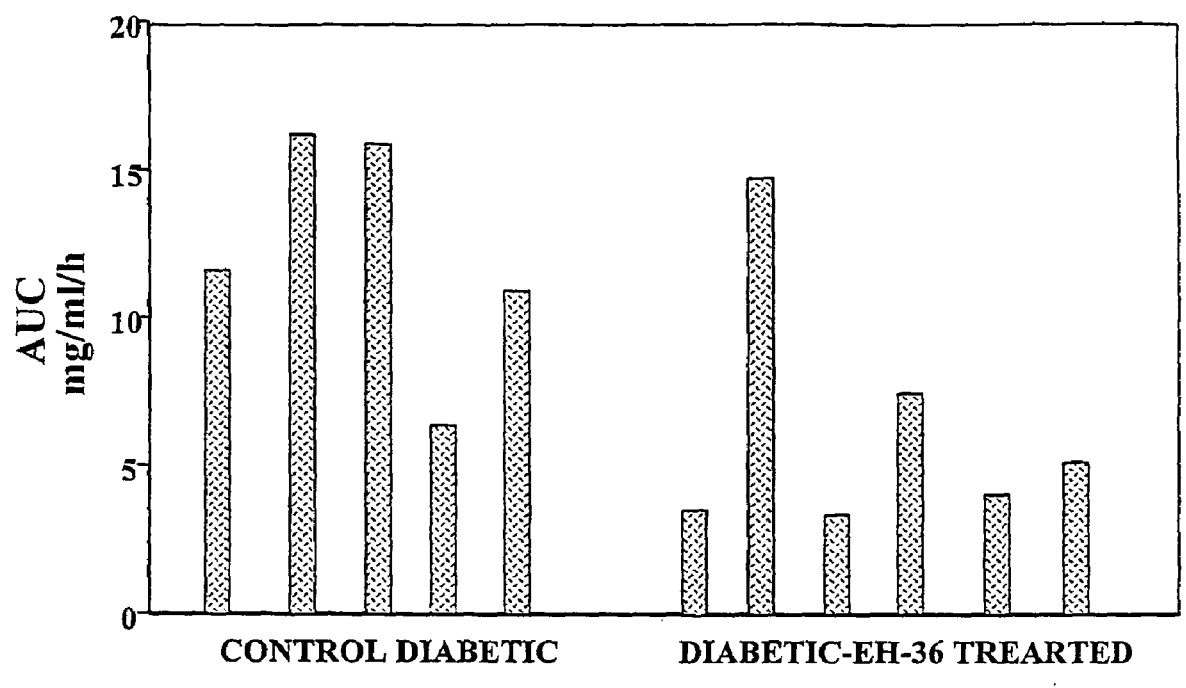

FIG. 13: Anti-hyperglycemic activity of EH-36 in streptozotocin-diabetic mice. Mice were treated with EH-36 (as described in the legend to FIG. 12) or the vehicle alone (sesame oil, bold lines), and their blood glucose levels were determined at the indicated time intervals. C57/black mice were made diabetic as described in the legend to FIG. 12.

Figure 14:
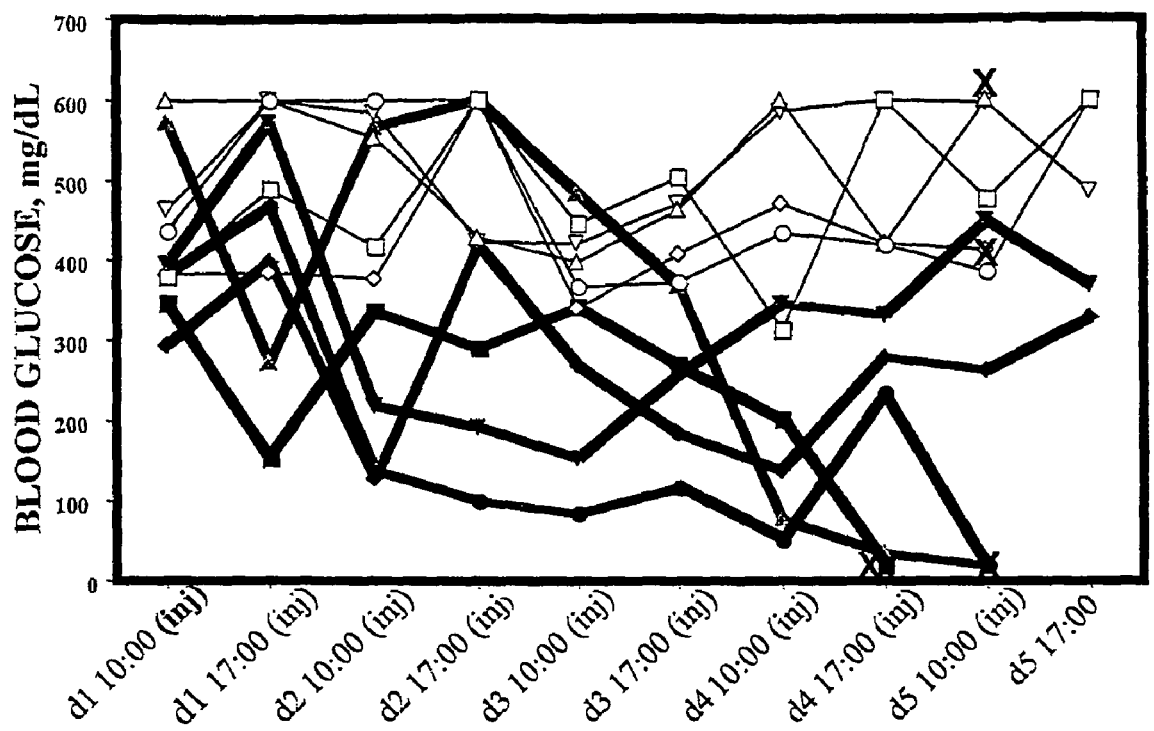

FIG. 14: Glucose tolerance test (GTT) of diabetic mice treated with sesame oil or EH-36 for 9 days, as described in the legend to FIG. 12. On the morning of the $10^{th}$ day and following an overnight fast the mice received glucose (2 gr/Kg body weight) by i.p. injection, Blood glucose was determined for 3 hr at 30 min intervals. The glucose data were plotted for each animal and the area under the curve (AUC) was calculated.

Figure 15:
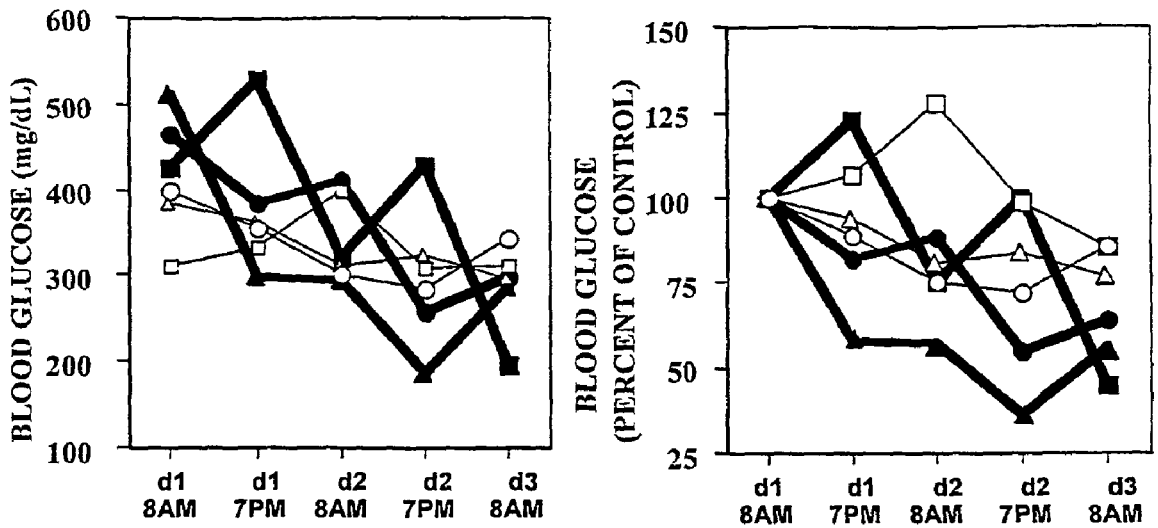

FIG. 15: Photographs of an oil-treated diabetic mouse (left) and EH-36-treated mouse.

Figure 16A:
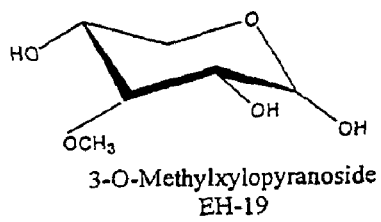
Figure 16A:
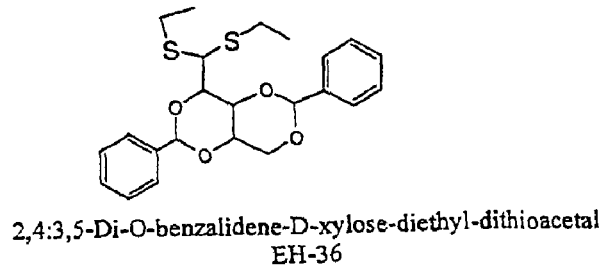
Figure 16A:
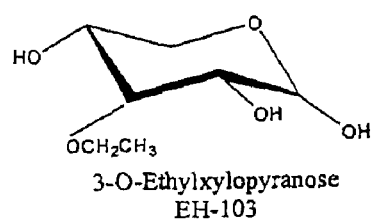
Figure 16A:
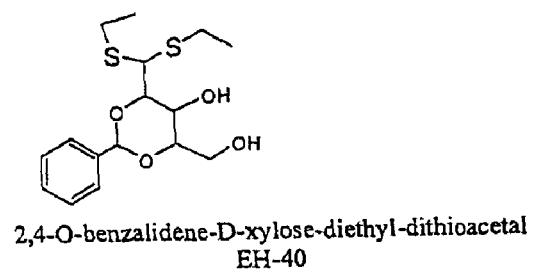
Figure 16A:
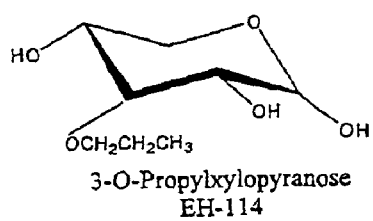
Figure 16A:
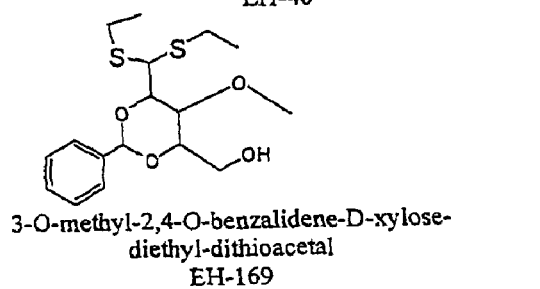
Figure 16A:
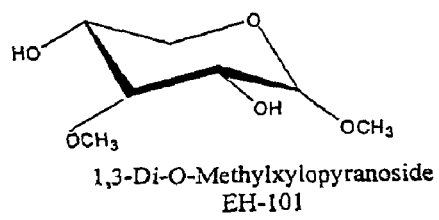
Figure 16A:
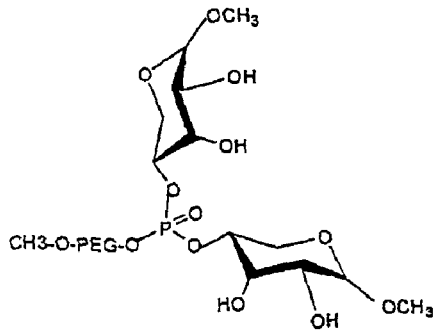
Figure 16B:
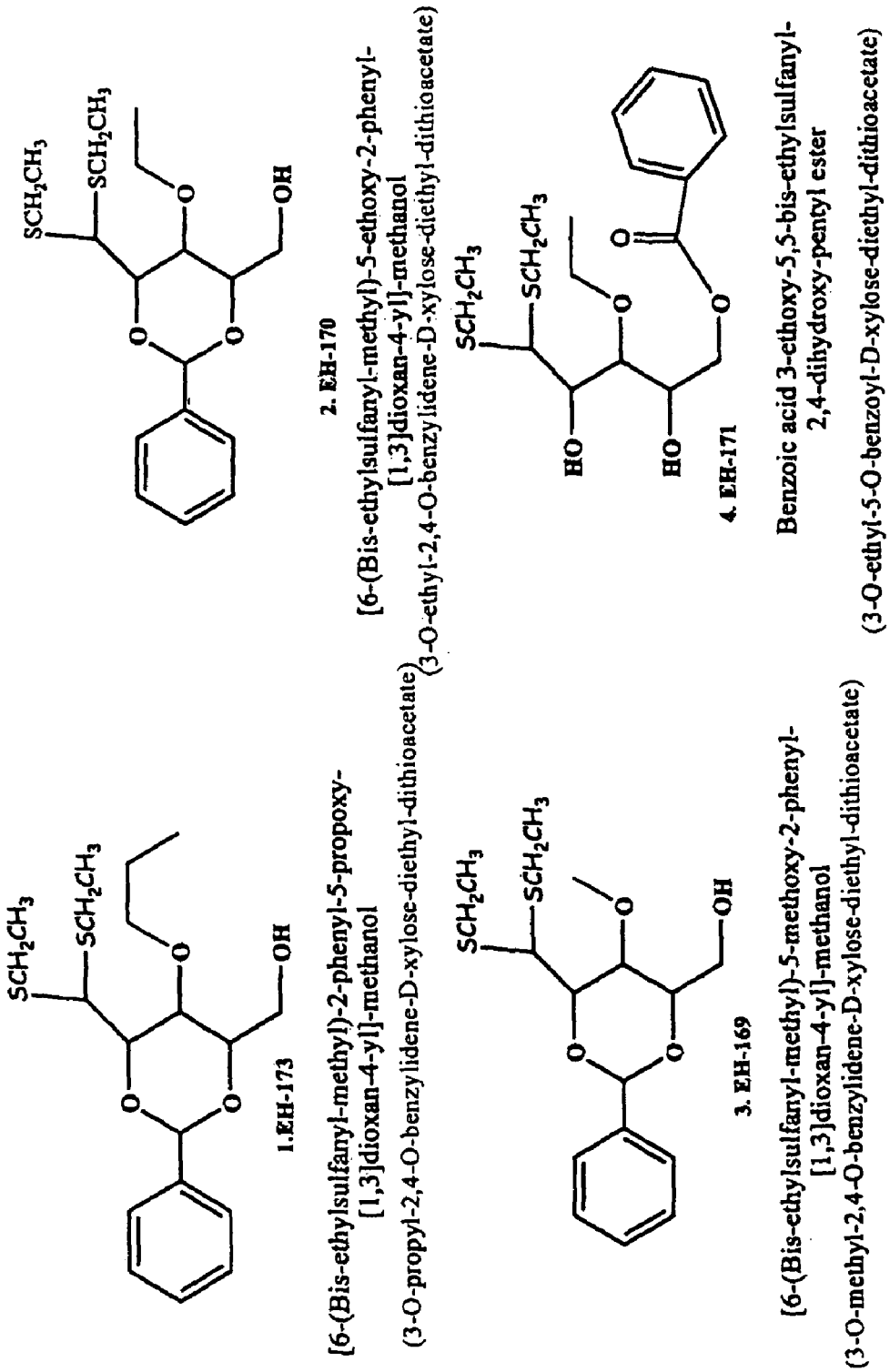
Figure 16C:
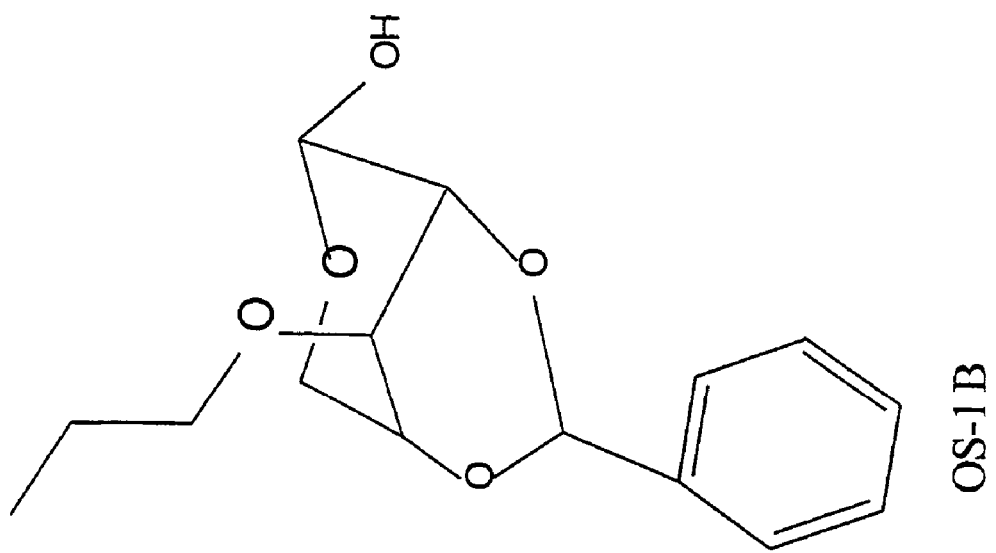
Figure 16C:
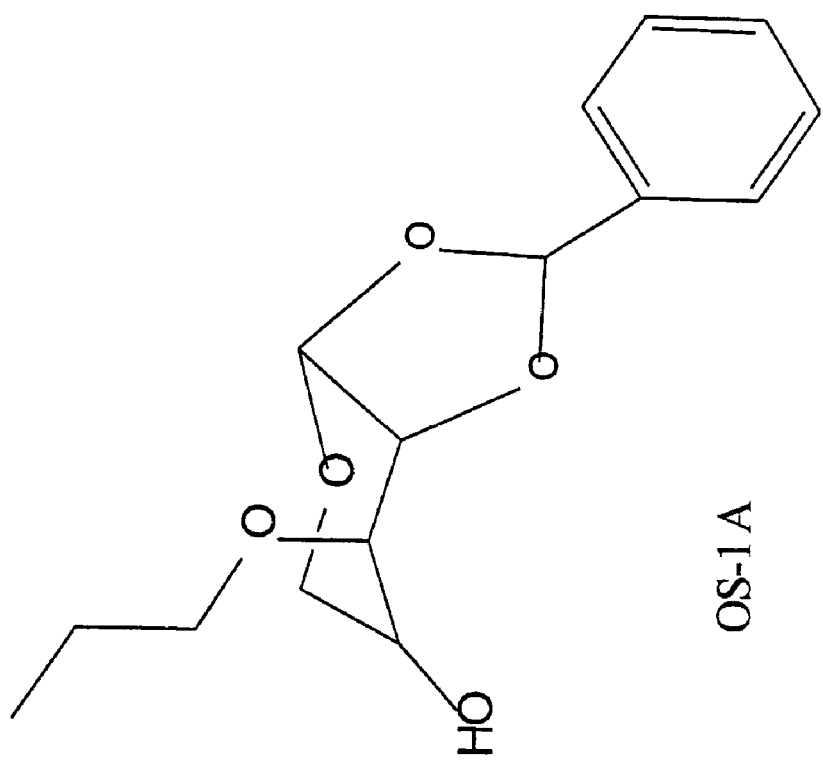

FIG. 16A:

FIG. 16B:

FIG. 16C: Structures of several novel pentose derivatives provided by the present invention.

DETAILED DESCRIPTION OF THE INVENTION

The present invention relates to pentose derivatives that are effective at increasing glucose transport in a non-insulin dependent manner, and to uses thereof for a) treating and/or preventing hyperglycemia; b) treating and/or preventing the complications of hyperglycemia; c) treating diabetes; d) increasing the rate of cellular glucose transport; e) increasing the rate of cellular glucose uptake; f) improving the ability of a subject to metabolize glucose; g) treating daily blood glucose fluctuations; h) reducing blood sugar levels; i) reducing the dosage of anti-diabetic medication needed for treatment of diabetes. The present invention further provides novel pentose derivatives having beneficial properties in terms of pharmacokinetics, to pharmaceutical compositions comprising these novel compounds and uses thereof.

Compounds

In one embodiment, the present invention provides novel pentose derivatives that are effective at increasing the rate of glucose transport, and in addition have beneficial properties in terms of pharmacokinetics, which makes them attractive as agents for treating and/or preventing hyperglycemia, complications arising therefrom, and diabetes. As contemplated herein, these novel pentose derivatives, or their pharmaceutically acceptable salts or hydrates thereof are represented by at least one of the structures of formulae I-III:

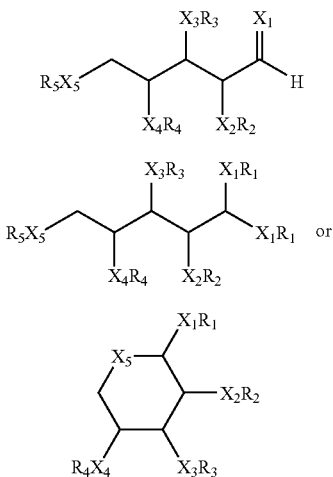

wherein

X$_1$ and X$_3$ are O or S;

R$_1$ and R$_3$ are independently of each other hydrogen, a C$_1$-C$_6$ alkyl, an O or S protecting group, or an amino acid containing a thiol or hydroxyl group in its side-chain;

X$_2$, X$_4$ and X$_5$ are independently of each other O, S, or NH;

R$_2$, R$_4$ and R$_5$ are independently of each other hydrogen or an O, S or N protecting group, provided that when X$_1$-X$_5$ are oxygen and R$_2$, R$_4$ and R$_5$ are hydrogen, at least one of R$_1$ and R$_3$ is other than hydrogen or methyl;

or a pharmaceutically acceptable salt, hydrate or derivative thereof.

In one embodiment, the pentose derivative is a xylose, ribose, arabinose or lyxose derivative. In one preferred embodiment, the pentose derivative is a xylose derivative. In another preferred embodiment, the pentose derivative is a D-xylose derivative. In yet another preferred embodiment, the pentose derivative is represented by the structure of formula I, i.e. an aldehyde or thioaldehyde. In another preferred embodiment, the pentose derivative is represented by the structure of formula II, i.e. an acetal or thioacetal. In another preferred embodiment, the pentose derivative is represented by the structure of formula III, i.e. a ring pyranoside or thiopyranoside.

In one embodiment, X1 in any of the formulae I-III is O. In another embodiment, X1 in any of the formulae I-III is S. In another embodiment, R1 in any of the formulae I-III is methyl. In another embodiment, R1 in any of the formulae I-III is ethyl. In another embodiment, R1 in any of the formulae I-III is propyl. In another embodiment, R1 in any of the formulae I-III is isopropyl. In one embodiment, X3 in any of the formulae I-III is O. In another embodiment, X$_3$ in any of the formulae I-III is S. In another embodiment, R3 in any of the formulae I-III is methyl. In another embodiment, R3 in any of the formulae I-III is ethyl. In another embodiment, R3 in any of the formulae I-III is propyl. In another embodiment, R3 in any of the formulae I-III is isopropyl. In another embodiment, X1 is S and R1 is methyl. In another embodiment, X$_1$ is S and R$_1$ is ethyl.

An "O-protecting group" is a protecting group used to protect carbohydrate hydroxyl groups. The protecting group can be for example an alkyl (e.g. methyl, ethyl), allyl or phenyl, resulting in an ether group, e.g. methyl ether, ethyl ether, allyl ether, phenyl ether and the like. The protecting group can also be an acyl (C(=O)R wherein R is an alkyl or phenyl), resulting in an ester group OC(=O)R n. In addition, the protecting group can be a ketone (e.g. acetone) or aldehyde (e.g. benzaldehyde). In this case two hydroxyls on different carbons are joined together to form an acetal or ketal.

An "S-protecting group" is a protecting group used to protect thiol groups. The protecting group can be for example an alkyl (e.g. methyl, ethyl), allyl or phenyl, resulting in a thioether group, e.g. methyl thioether, ethyl thioether, allyl thioether, phenyl thioether and the like. The protecting group can also be an acyl (C(=O)R wherein R is an alkyl or phenyl), resulting in a thioester group SC(=O)R. In addition, the protecting group can be a ketone (e.g. acetone) or aldehyde (e.g. benzaldehyde). In this case two thiols on different carbons are joined together to form a thioacetal or thioketal.

An "N-protecting group" is a protecting group used to protect NH groups. The protecting group can be for example an alkyl (e.g. methyl, ethyl), allyl or phenyl, resulting in an allcylamine e.g. methylamine, ethylamine, allylamine, phenylamine and the like. The protecting group can also be an acyl (C(=O)R wherein R is an alkyl or phenyl), resulting in an amide group NHC(=O)R. In addition, the protecting group can be a ketone (e.g. acetone) or aldehyde (e.g. benzaldehyde).

Also contemplated by the present invention is the use of mixed ketal and acetal protecting groups, formed from reaction of a hydroxyl and a thiol, hydroxyl and amine, or thiol and amine, with a ketone or an aldehyde, A suitable protecting group for the compounds of the present invention is a benzylidene (—CH-phenyl) moiety. A benzylidene acetal is formed from a reaction of hydroxyls with benzaldehyde. A benzylidene thioacetal is formed from a reaction of thiols with benzaldehyde. Other suitable protecting groups include hexalidene, pentalidene and octalidene, formed from a reaction with hexa-, penta- or octaldehyde. An acetonide or thioacetonide moiety formed by reaction with acetone is also contemplated by the present invention.

In one embodiment of Formulas I-III, any one or more of a) R$_1$ together with R$_2$; b) R$_1$ together with R$_3$; c) R$_2$ together with R$_3$; d) R$_2$ together with R$_4$; e) R$_3$ together with R$_4$; f) R$_3$ together with R$_5$; or g) R$_4$ together with R$_5$, independently of each other represent a CR$_6$R$_7$ group wherein R$_6$ and R$_7$ are independently of each other a hydrogen, a linear or branched-chain alkyl or a phenyl.

A preferred protecting group for the present invention is a benzylidene moiety, formed by reaction of the hydroxyls, thiols or amines with benzaldehyde. It is understood that when one of R$_6$ and R$_7$ represent a hydrogen and the other represents a benzyl, the CR$_6$R$_7$ group is a benzylidene group.

In one preferred embodiment of formulas I-III, R$_2$ together with R$_4$ represent a CH-phenyl group, i.e. a benzylidene moiety. In another preferred embodiment, R$_3$ together with R$_5$ represent a CH-phenyl group. In another preferred embodiment, both R$_2$ together with R$_4$ and R$_3$ together with R$_5$ each represent a CH-phenyl group. In another preferred embodiment, R$_1$ together with R$_2$ represent a CH-phenyl group.

In one embodiment of Formulas I-III, R$_1$ and/or R$_3$ are an amino acid containing a thiol or hydroxyl group in its side-chain. Such amino acids include but are not limited to cysteine, homocysteine, serine, homoserine, threonine, homothreonine, hydroxyproline, tyrosine and un-natural amino acids which contain thiol or hydroxyl groups in side-chains.

In another embodiment, the present invention provides a methoxy-polyethyleneglycol (PEG) derivative of any one or more of the pentoses provided herein.

An "alkyl" group refers to a saturated aliphatic hydrocarbon, including straight-chain, branched-chain and cyclic alkyl groups. In one embodiment, the alkyl group has 1-12 carbons. In another embodiment, the alkyl group has 1-10 carbons. In another embodiment, the alkyl group has 1-7 carbons. In another embodiment, the alkyl group has 1-6 carbons. In another embodiment, the alkyl group has 1-4 carbons. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

In one embodiment, the pentose derivative is a xylose derivative. In another embodiment, the pentose is represented by the structure of formula I, i.e. an aldehyde or thioaldehyde. In another embodiment, the pentose is represented by the structure of formula II, i.e. an acetal or thioacetal. In another embodiment, the pentose is represented by the structure of formula III, i.e. a ring pyranoside or thiopyranoside.

In another embodiment, the present invention provides a pentose represented by at least one of the structures of formulae IV-V:

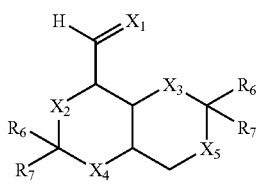

IV

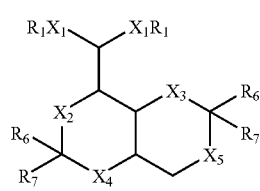

V wherein $X_1$-$X_5$, and $R_1$ are defined above, and $R_6$ and $R_7$ are independently of each other hydrogen alkyl or phenyl.

In yet another embodiment, the present invention provides a pentose represented by at least one of the structures of formulae VI-VII:

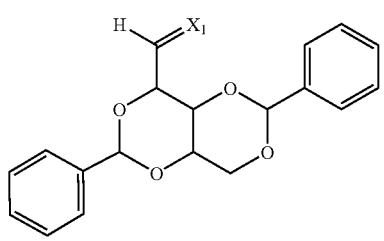

VI

-continued

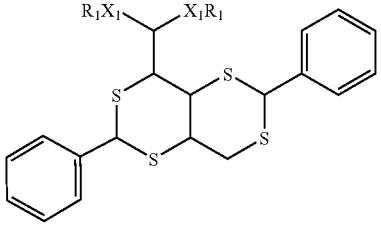

VII wherein $X_1$ and $R_1$ are as defined above.

As contemplated herein, specific non-limiting examples of the pentoses that are included within the scope of the present invention are: di-4-O-(1-O-methyl-α-xylopyranoside)-phosphoryl-O-methyl-PEG; 2,4:3,5-di-O-benzylidene-D-xylose-dimethylacetal; 2,4:3,5-di-O-benzylidene-D-xylose-diethyl-dithioacetal; 3-O-ethyl-2,4-O-benzylidene-D-xylose-diethyl-dithioacetal; propyl-thio-β-xylopyranoside; ethyl-thio-β-xylopyranoside; lauryl-thio-β-xylopyranoside; D-xylose-di-N-acetylcysteine-dithioacetal; D-xylose-di-cysteine-dithioacetal; D-xylose-diethyl-dithioacetal; D-xylose-dipropyl-dithioacetal; 1,3-O-dimethylxylopyranoside; 2,4-benzylidene-D-xylose-diethyl-dithioacetal; 3-O-methyl-2,4-O-benzylidene-D-xylose-diethyl-dithioacetal, 3-O-propyl-2,4-O-benzylidene-D-xylose-diethyl-dithioacetal, 3-O-ethyl-5-O-benzoyl-D-xylose-diethyl-dithioacetal, 3-O-propyl-1,2-benzylidene-D-xylose and 3-O-propyl-2,4-benzylidene-D-xylose. It is understood that these examples are provided in order to set forth different embodiments of the present invention, and should not be construed in any way as limiting the broad scope of the pentoses provided by the present invention.

In one embodiment, the present invention comprises administering a pharmaceutically acceptable salt of the pentose and pentose derivatives of the present invention. The term "pharmaceutically acceptable salt" includes acid addition salts which are formed with inorganic acids such as, for example, hydrochloric or phosphoric acids, or such organic acids as acetic, oxalic, tartaric, mandelic, and the like. The term also includes base addition salts which are formed from inorganic bases such as, for example, sodium, potassium, ammonium, and calcium, and from organic bases such as isopropylamine, trimethylamine, histidine, and the like.

In another embodiment, the present invention comprises administering a hydrate of the pentose of the present invention. The term "hydrate" includes but is not limited to hemihydrate, monohydrate, dihydrate, trihydrate and the like. In another embodiment, the present invention comprises administering a derivative of the pentose, for example and without being limited to a PEG derivative (methoxy-polyethyleneglycol), a lipophilic derivative, a hydrophilic derivative, or any combination thereof.

Biological Activity of Pentose Derivatives

As described above, in the course of studying the intracellular mechanisms, which are operative in glucose autoregulation of the glucose transport system, the inventors have unexpectedly found that pentose derivatives, and D-xylose derivatives in particular as described herein, increase the rate of glucose transport in skeletal muscle cells and adipocytes in a non-insulin dependent manner. As demonstrated herein, D-xylose and derivatives thereof enter the cells and stimulates rapidly and markedly the glucose transport system. This effect of D-xylose and its derivatives is dose- and time-dependent. It induced maximal upregulation of hexose transport in L8 and C2 myocytes, in L6 myotubes and in 3T3-L1 adipocytes in culture.

The mechanism of action of xylose is not yet clear, however the clinical utility of the present disclosure is not bound by any particular theory or mechanism of action. Unlike the vast literature on glucose metabolism less is known about xylose. However, the following studies and discoveries point out that this pentose is metabolized in cells, incorporated into glycogen, participated in xylolysation of proteoglycans, regulates the expression and activity of major enzymes in glucose and fatty acid metabolism. The liver also can transform D-xylose into D-xylitol and D-xylonic acid. It has been proven that both D-xylose and D-xylitol can be used as sole carbon source in mammalian cells, and that the enzyme xylulokinase is induced under this condition [Demetrakopoulos, G. E. and Amos, H. (1976) Biochem. Biophys. Res. Commun. 72, 1169-1178]. Moreover, in vivo conversion of D-xylitol to glycogen via the pentose phosphate pathway and even D-xylose oxidation to carbon dioxide have been reported [McCormick, D. B. and Touster, O. (1958) J. Biol. Chem. 226:451-461]. In rat liver cytosol xylose oxidation is regulated by glucose-6-phosphate dehydrogenase [Metzger, R. et al. (1972) Arch. Biochem. Biophys. 149, 102-109]. Moreover, transcriptional glucose signaling through the glucose response element was found to be mediated by the pentose phosphate pathway [Doiron, B. et al. (1996) J. Biol. Chem. 271, 5321-5324]. In addition the enzyme xylosyltransferase catalyses the transfer of xylose from UDP-xylose to consensus serine residues of proteoglycan core proteins [Brinkman, T. et al. (1997) J. Biol. Chem. 272, 11171-11175]. Quite interesting is the observation that xylitol induces the expression of fatty acid synthase in cultured rat hepatocytes in a glucose-6-phosphate concentration-dependent manner Mourrieras, F. et al. (1997) Biochem. J. 326, 345-349]. D-xylose can also affect glucose metabolism by the, activity of xylulose-5-phosphate-activated protein phosphatase that catalyzes dephosphorylation of fructose-2,6-bisphosphatase [Nishimura, M. and Uyeda, K. (1995) J. Biol. Chem. 270, 26341-26346].

Thus, in one embodiment, the present invention provides a method of preventing or treating hyperglycemia in a subject, comprising the step of administering to the subject a pentose or pentose derivative, in an amount effective to lower blood glucose levels in the subject, thereby preventing or treating hyperglycemia in the subject.

In another embodiment, the present invention provides a method of preventing or treating a complication of hyperglycemia in a hyperglycemic subject, the method comprising the step of administering to the subject a pentose or pentose derivative, in an amount effective to lower blood glucose levels in the subject, thereby preventing or treating the complication of hyperglycemia in the subject. Non-limiting examples of complications of hyperglycemia are cardio-vascular disease, diabetic neuropathy, nephropathy, retinopathy, glaucoma, cataract, diabetic ketoacidosis, lactic acidosis, and insulin resistance.

The term "cardio-vascular disease" means a disease pertaining to blood vessels or indicative of abnormal blood supply and structural and functional abnormalities of the heart and blood vessels. The term "neuropathy" means functional disturbances and/or pathological changes in the peripheral nervous system. "Diabetic neuropathy" is a condition that is caused by long-standing or poorly controlled diabetes, and is manifested by peripheral and autonomic nerve dysfunction. The term "retinopathy" means vascular changes that lead to degeneration of the retina. The term "glaucoma" refers to a group of eye diseases characterized by an increase in intraocular pressure, which causes pathological changes in the optic disk and typical defects in the field of vision. The term "cataract" means an ocular opacity, partial or complete, of one or both eyes, or in the lens or capsule, especially an opacity impairing vision or causing blindness. The term "diabetic ketoacidosis" refers to a complication of diabetes, which is manifested by acidosis accompanied by the accumulation of ketone bodies (ketosis) in the body tissue and fluids. The term "lactic acidosis" means acidosis caused by accumulation of lactic acid more rapidly than it can be metabolized. Lactic acidosis can occur spontaneously or in association with diseases such as diabetes mellitus. The term "insulin resistance" means a condition in which a subject produces insulin, but his/her body does not respond to the action of insulin. Insulin resistance is linked to hyperglycemia, overweight, high blood pressure and high levels of fat in the blood.

Furthermore, in another embodiment, the present invention provides a method of treating diabetes in a subject, comprising the step of administering to the subject a pentose or pentose derivative, in an amount effective to lower blood glucose levels in the subject, thereby treating diabetes in the subject. In one embodiment, the diabetes is diabetes mellitus. In another embodiment, the diabetes is insulin-dependent diabetes mellitus (Type-I diabetes). In yet another embodiment, the diabetes is non-insulin-dependent diabetes mellitus (Type-II diabetes).

The term "diabetes" means a relative or absolute lack of insulin or insulin activity leading to uncontrolled carbohydrate metabolism. Most patients can be clinically classified as having either insulin-dependent diabetes mellitus (IDDM or Type-I diabetes) or non-insulin-dependent diabetes mellitus (NIDDM or Type-II diabetes).

Furthermore, in another embodiment, the present invention provides a method of increasing the rate of cellular glucose transport in a subject, comprising the step of administering to the subject a pentose derivative of the present invention, in an amount effective to increase the rate of cellular glucose transport in the subject.

Furthermore, in another embodiment, the present invention provides a method for improving the ability of a subject to metabolize glucose, the method comprising administering to the subject a pentose or pentose derivative, in an amount effective to improve the ability of a subject to metabolize glucose.

Furthermore, in another embodiment, the present invention provides a method for treating daily blood glucose fluctuations in a subject susceptible to daily blood glucose fluctuations, the method comprising administering to the subject a pentose or pentose derivative, in an amount effective to treat daily blood glucose fluctuations in a subject susceptible to daily blood glucose fluctuations.

Furthermore, in another embodiment, the present invention provides a method for reducing blood sugar levels in a subject susceptible to abnormal fluctuations in blood sugar levels, the method comprising administering to the subject a pentose or pentose derivative, in an amount effective to reduce blood sugar levels in a subject susceptible to abnormal fluctuations in blood sugar levels.

Furthermore, in another embodiment, the pentoses and pentose derivatives of the present invention can be used also in a combination therapy with insulin in Type 1 (and Type 2) diabetic patients, in order to reduce the daily insulin requirement and for a better control of temporal fluctuations in blood glucose, which are often observed in these patients. Thus the present invention also provides a method for reducing the dosage of anti-diabetic medication needed for treatment of a diabetic subject, the method comprising administering to the subject a pentose or pentose derivative, in an amount effective to reduce the dosage of anti-diabetic medication needed for treatment of a diabetic subject. In accordance with this particular embodiment, the pentoses of the present invention may be administered in combination with one or more anti-diabetic agents, such as, for example insulin in Type 1 diabetes (or insulin in Type 2 diabetes treated with this hormone). The ability of the pentose to promote glucose transport and uptake will reduce the dosage of the anti-diabetic medication, which the pentose is administered with, and will enable to control fluctuations in blood glucose levels throughout the day.

In one embodiment, the subject treated by the methods of the present invention is a mammalian subject. In another embodiment, the subject is a human subject. In another embodiment, the subject is a non-human mammal.

Furthermore, in one embodiment, the present invention provides a method of increasing the rate of glucose transport in a cell, comprising the step of contacting the cell with a pentose or pentose derivative, in an amount effective to increase the rate of glucose transport in the cell. In another embodiment, the present invention provides a method of increasing the rate of glucose uptake by a cell, comprising the step of contacting the cell with a pentose or pentose derivative, in an amount effective to increase the rate of glucose transport in the cell. In one embodiment, the cell is a mammalian cell. In another embodiment, the cell is a human cell.

In one embodiment, the pentose that is effective at a) treating and/or preventing hyperglycemia; b) treating and/or preventing a complication or hyperglycemia; c) treating diabetes; d) increasing the rate of cellular glucose transport; e) increasing the rate of cellular glucose uptake; f improving the ability of a subject to metabolize glucose; g) treating daily blood glucose fluctuations; h) reducing blood sugar levels i) reducing the dosage of anti-diabetic medication needed for treatment of diabetes; j) increasing the rate of glucose transport in a cell; and/or k) increasing the rate of glucose uptake by a cell, is selected from xylose, ribose, arabinose and lyxose. In another embodiment, the pentose is a deoxypentose, for example deoxyxylose, deoxyribose, deoxyarabinose or deoxylyxose.

In one embodiment, the pentose is a D-pentose. In a preferred embodiment, the pentose is xylose. In another preferred embodiment, the pentose is D-xylose. In another embodiment, the pentose derivative is a compound of formula I, II or III as described herein.

As demonstrated in the Examples hereinbelow, D-xylose by itself has unfavorable pharmacokinetic and pharmacodynamic parameters. The concentrations required to achieve its biological effects are high and its duration of action is short. The present invention therefore further provides certain prototype drugs based on the chemical structure of D-xylose in order to increase its lipid solubility and prolong its duration of action.

Pharmaceutical Compositions

In one embodiment, the pentose of the present invention is administered as a pharmaceutical preparation comprising the pentose, and a pharmaceutically acceptable carrier. As used herein, "pharmaceutical preparation" or "pharmaceutical compositions", used herein interchangeably, means a "therapeutically effective amount" of the pentose. A "therapeutically effective amount" as used herein refers to that amount which provides a therapeutic effect for a given condition and administration regimen.

In one embodiment, pharmaceutical preparation is orally administered in solid or liquid dosage form. In another embodiment, the pharmaceutical preparation is intravenously, intraarterially, subcutaneously, intradermally, intraperitoneally, intramuscularly or intralesionally injected in liquid form. In another embodiment, the pharmaceutical preparation is administered as an intravaginal ring. In another embodiment, the pharmaceutical preparation is formulated as a topical formulation for topical application. In another embodiment, the pharmaceutical preparation is a pellet, a tablet, a capsule, a solution, a suspension, an emulsion, a gel, a cream, a depot, a suppository, an intra-vaginal ring, or a parenteral formulation In a particular preferred embodiment the pharmaceutical preparation is formulated as a depot for providing sustained release of the active ingredient.

In one embodiment, the pharmaceutical preparations are administered orally, and are thus formulated in a form suitable for oral administration, i.e. as a solid or a liquid preparation. Suitable solid oral formulations include tablets, capsules, pellets and the like. Suitable liquid oral formulations include solutions, suspensions, emulsions, and the like.

Further, in another embodiment, the pharmaceutical preparations are administered by intravenous, intraarterial, intraperitoneal, subcutaneous, intradermal, intramuscular or injection of a liquid preparation. Suitable liquid formulations include solutions, suspensions, emulsions, and the like. Particularly preferred embodiment include depots providing sustained release or prolonged duration of activity of the active ingredient in the subject.

Further, in another embodiment, the pharmaceutical compositions are administered topically to body surfaces, and are thus formulated in a form suitable for topical administration. Suitable topical formulations include gels, ointments, creams, lotions, and the like. Further, in another embodiment, the pharmaceutical compositions are administered as a suppository, for example a rectal suppository or a vaginal or urethral suppository. Further, in another embodiment, the pharmaceutical compositions can be applied on conventional intravaginal rings or other intravaginal devices.

As used herein a "pharmaceutically acceptable carrier" may be a solid carrier for solid formulations, a liquid carrier for liquid formulations, or mixtures thereof. Solid carriers include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof. For liquid formulations, pharmaceutically acceptable carriers may be aqueous or non-aqueous solutions, suspensions, or emulsions. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media.

Parenteral vehicles (for subcutaneous, intravenous, intraarterial, intraperitoneal or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

In addition, the compositions may further comprise binders (e.g. cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g. glycerol, polyethylene glycerol), anti-oxidants (e.g. ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g. Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g. poloxamers or poloxamines), coating and film forming agents (e.g. ethyl cellulose, acrylates, polymethacrylates) and/or adjuvants.

In one embodiment, the pharmaceutical compositions provided herein are controlled release compositions, i.e. compositions in which the pentose is released over a period of time after administration. In another embodiment, the composition is an immediate release composition, i.e. a composition in which all of the pentose is released immediately after administration.

The preparation of pharmaceutical compositions which contain an active component is well understood in the art, for example by mixing, granulating, or tablet-forming processes. The active therapeutic ingredient is often mixed with excipients, which are pharmaceutically acceptable and compatible with the active ingredient. For oral administration, the pentose is mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the pentose is converted into a solution, suspension, or emulsion, if desired with the substances customary and suitable for this purpose, for example, solubilizers or other.

As used herein, the term "administering" refers to bringing a subject in contact with a pharmaceutical composition comprising the pentose of the present invention. As used herein, administration can be accomplished in vitro, i.e. in a test tube, or in vivo, i.e. in cells or tissues of living organisms, for example humans. As used herein, the term "treating" means remedial treatment, and encompasses the terms "reducing", "suppressing" "ameliorating" and "inhibiting", which have their commonly understood meaning of lessening or decreasing. The term "preventing" means inhibiting the disease or condition, so that the disease or condition does not develop or progress.

As used herein, the term "contacting" means that the pentose and pentose derivatives of the present invention are introduced into a sample containing the enzyme, receptor or structural or vesicular proteins in a test tube, flask, tissue culture, chip, array, plate, microplate, capillary, or the like, and incubated at a temperature and time sufficient to permit binding of the pentose to the enzyme, receptor or structural or vesicular proteins. Methods for contacting the samples with the pentose or other specific binding components are known to those skilled in the art and may be selected depending on the type of assay protocol to be run. Incubation methods are also standard and are known to those skilled in the art.

In another embodiment, the term "contacting" means that the pentose or pentose derivatives of the present invention are introduced into a subject receiving treatment, and the pentose is allowed to come in contact with its receptor in vivo.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

Experimental Details Section

EXAMPLE 1

Effect of D-xylose on Glucose Transport in vitro

The time-course of D-xylose effect in two types of skeletal muscle cells (L8 myocytes and C2 myotubes) was studied. L8 myocytes and C2 myotubes preconditioned in 20 mM glucose were incubated with 20 mM xylose. After 90 min the cells were washed and incubated with 20 mM glucose, and subjected to a deoxyglucose dGlc uptake assay (14).

Figure 1:
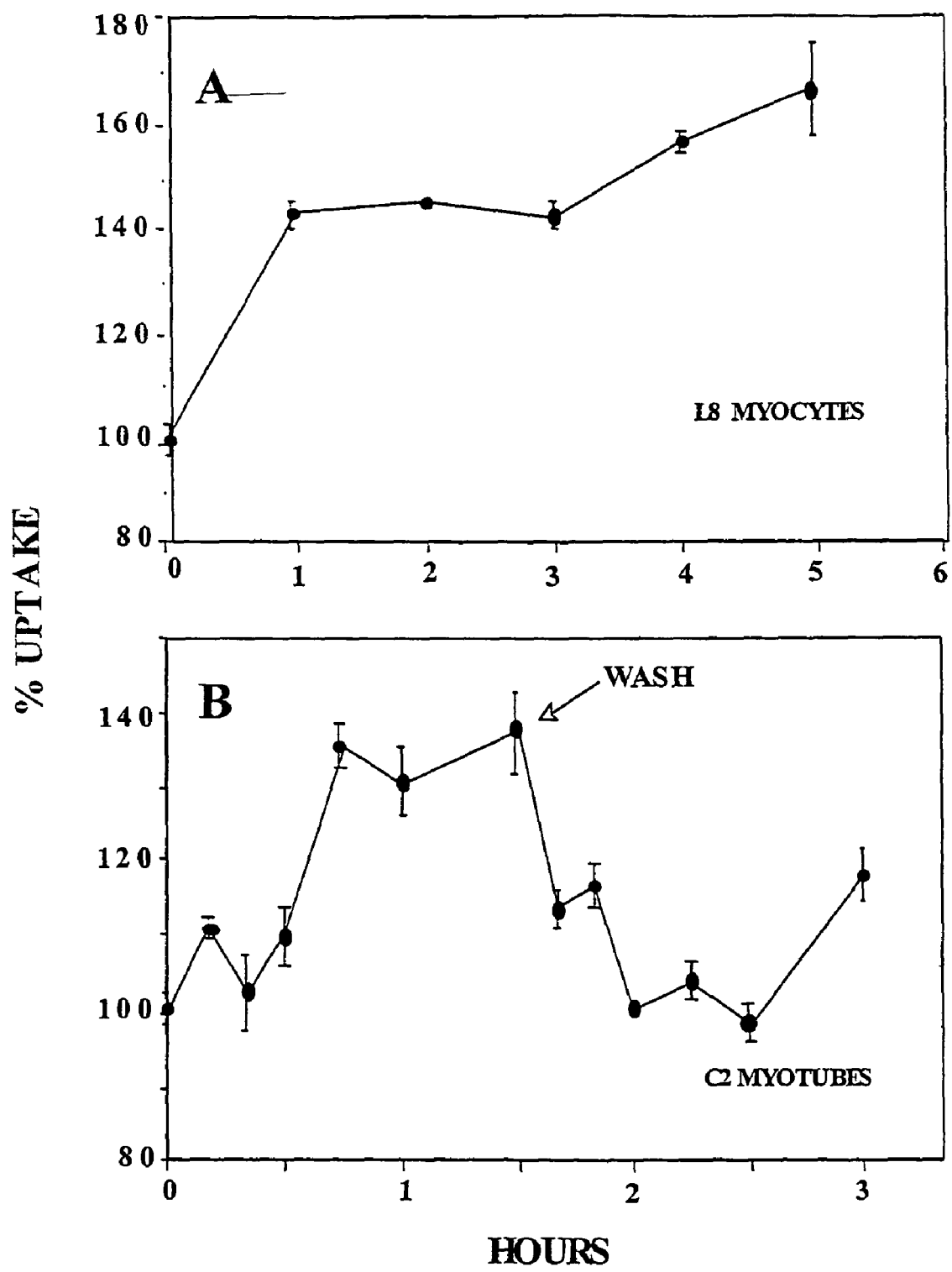
FIG. 1: Effect of D-xylose on glucose transport in L8 myocytes and C2 myotubes. L8 myocytes and C2 myotubes preconditioned in 20 mM glucose were incubated with 20 mM xylose. After 90 min the cells were washed and incubated with 20 mM glucose. Control dGlc ([$^3$H]-2-deoxy-D-glucose; dGlc) uptake values: A: 62.3±4.5 pmol/million cells/min; B: 592.2±19.0 pmol/mg protein/min. Mean±SEM (n=3)

The results are depicted in FIG. 1. The results show that D-xylose increases the rate of glucose transport in L8 myocytes and C2 myotubes. The results also show that the stimulatory effect of D-xylose is dependent on its presence in the culture medium; once washed the rate of hexose uptake declined rapidly to the control level.

Figure 2:
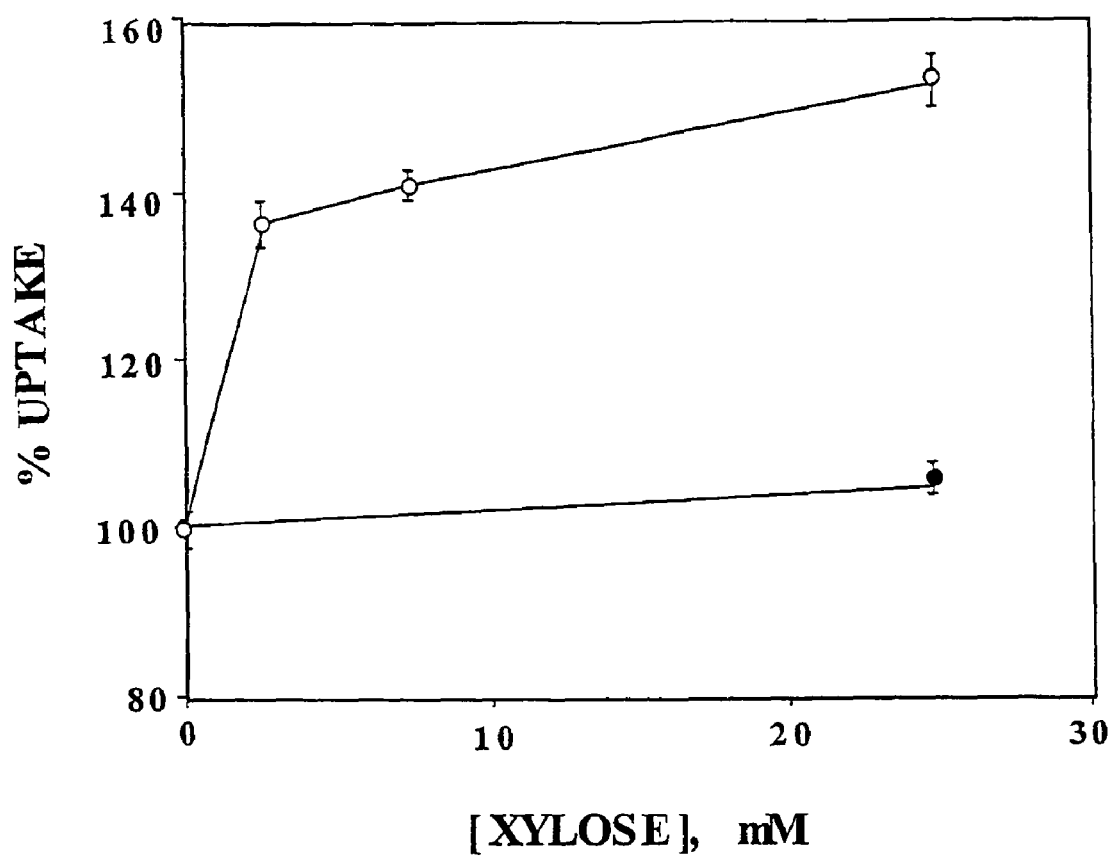
FIG. 2: Dose-response curve of D-xylose effect in C2 myotubes. C2 myotubes preconditioned with 20 mM glucose received fresh medium containing 20 mM glucose (black circle) or the indicated concentrations of xylose (open circle). dGlc uptake assay was performed after 1 hr incubation. 100%=0.84±2.1 nmol dGlc/mg protein/min. Mean±SEM (n=3).

The inventors have also measured the effect of different doses of D-xylose in C2 myotubes. C2 myotubes preconditioned with 20 mM glucose received fresh medium containing 20 mM glucose or increasing concentrations of D-xylose. Standard dGlc uptake assay was performed after 1 hr incubation. The dose-response curve of D-xylose effect in C2 myotubes (FIG. 2) shows that maximal effect is obtained at 20 mM D-xylose. D-xylose augmented the rate of hexose transport ~2-fold within 1-2 hr; half-maximal stimulation was observed within 20-30 min, as shown in FIG. 2.

In further experiments the inventors used 20 mM D-xylose to induce maximal effects without increasing significantly the osmolarity of the culture medium (cells incubated with 20 mM sucrose had uptake levels similar to the control cells).

Kinetic analysis revealed that D-xylose increases the Vmax of the hexose transport system without changing the Km (data not shown). The stimulatory effect of D-xylose lasts as long as it was present in the culture medium; once washed the rate of hexose uptake declines rapidly to the control level.

Figure 3:
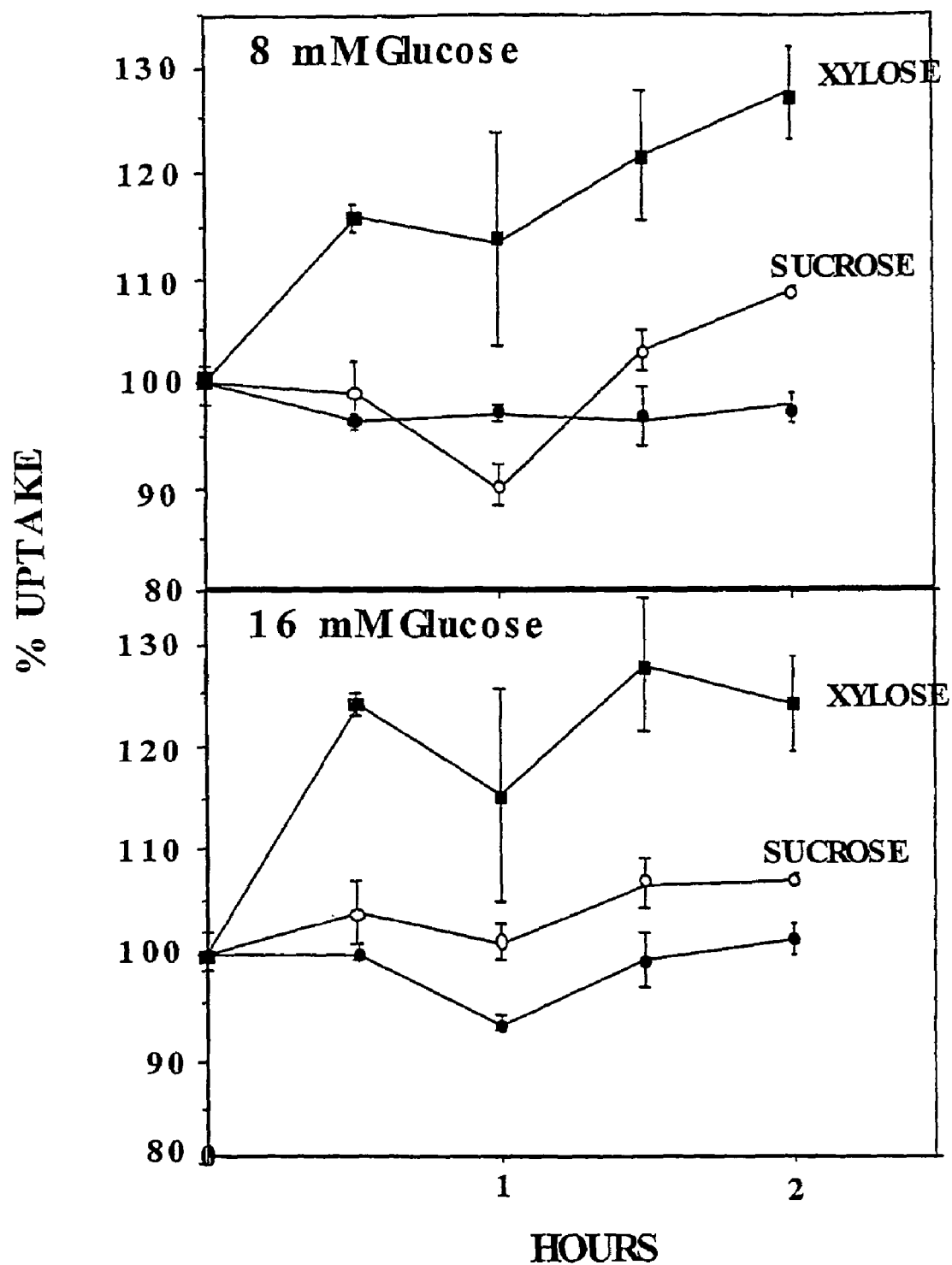
FIG. 3: Effect of D-xylose on C2 myotubes in the presence of glucose. C2 myotubes were incubated with 8 or 16 mM glucose in the absence (black circle) or in the presence of 20 mM sucrose (open circle) or xylose (black rectangle). At the indicated times the cells were analyzed for dGlc uptake assay. Mean=SEM (n=3).

In C2 myotubes, whether up- or downregulated by preexposure to low or high glucose concentrations, respectively, D-xylose (20 mM) effectively increased the rate of hexose transport in a time-dependent manner. However, in the above experiments the cells were exposed to D-xylose after removal of the conditioning glucose concentration. This experimental protocol does not mimic the in vivo condition where a potential drug is given to hyperglycemic individuals. The inventors therefore added 20 mM D-xylose to C2 myotubes in the presence of 8 or 16 mM glucose and followed its effect. The results of these experiments attest to the ability of D-xylose to augment hexose transport in the presence of varying concentrations of glucose, as shown in FIG. 3.

It has shown before by the inventors of the present invention that deoxyglucose (dGlc) depresses the hexose transport system in myocytes and that a subsequent incubation with low (even no) glucose fails to reverse this effect of dGlc [Sasson, S et al (1997)]. The inventors have therefore measured the effect of D-xylose on rate of hexose transport following treatment with dGlc. In one experiment, C2 myotubes preconditioned with 2 mM glucose received fresh medium containing 2 mM dGlc. A portion of the cells were washed after 30 min and received 20 MM D-xylose or 2 mM D-glucose, and subjected to a dGlc uptake assay at different time points. In another experiment, L8 myocytes preconditioned with 2 mM glucose were washed and incubated with 2 mM xylose or 2 mM dGlc. A portion of the cells were washed again after 2 hr and incubated with 20 mM xylose, and subjected to a dGlc uptake assay at different time points.

As shown in FIG. 4, in C2 myotubes (FIG. 4A) and in L8 myocytes (FIG. 4B) D-xylose increased the rate of hexose transport downregulated by 30 min or 2 hr treatment with dGlc.

Thus, the upregulatory effect of D-xylose is different from that of simple glucose withdrawal. These findings suggest that D-xylose, which increases the rate of hexose transport in skeletal muscle, can serve as the basis for the development of new antihyperglycemic agents by virtue of their ability to reverse the downregulatory effect of hyperglycemia.

Since the standard hexose transport assay utilizes 0.1 mM dGlc in the presence of tracer amount of [$^3$H] dGlc, the inventors asked whether the results shown above were limited to this particular assay condition. Therefore, experiments were repeated with 10 mM dGlc in the uptake assay. However, since this high concentration of the cold glucose analogue markedly reduced the sensitivity of the assay, the inventors developed a non-radioactive, fluorimetric assay to determine the intracellular concentration of dGlc-6-P [Sasson, S. et al. (1993) *Anal. Biochem.* 215, 309-311]. The uptake of hexose under these assay conditions was also linear up to 25 min. The data show that at high hexose level D-xylose does not compete for transport via the glucose transporter.

In addition, the inventors investigated whether D-xylose is able to penetrate the cells. C2 myotubes conditioned with 2 mM glucose were washed and subjected to a [$^{14}$C]xylose uptake assay (0.1 mM xylose). As shown in FIG. 5, D-xylose itself is taken up by the cells.

The inventors have also determined the affinity of D-xylose for the glucose transporter. C2 myotubes preconditioned with 20 mM glucose were subjected to [$^3$H]dGlc uptake assay (0.1 mM dGlc) in the presence of increasing concentrations of unlabeled dGlc, glucose or xylose. The results of these experiments are depicted in FIG. 6. The affinity of D-xylose for the glucose transporter is 2 orders of magnitude lower compared to glucose. The final concentration of dGlc in the assay was 0.1 mM. Glucose and dGlc competed markedly and similarly with [$^3$H[dGlc, while D-xylose was a much weaker competitor, at least 100-fold molar excess being necessary to achieve 50% inhibition of transport.

Because of the high concentration of D-xylose required to produce its effects, the inventors screened for other pentoses that might mimic the effect of D-xylose. Indeed, D-arabinose, and to a lesser extent D-ribose and D-lyxose, showed similar effects as D-xylose. Yet, the most effective pentose to consistently increase the rate of hexose transport in skeletal muscle cells was D-xylose, as shown in FIG. 7.

This conclusion is also supported by the finding of the a better ability of D-xylose than the other pentoses to reverse 2-deoxy-D-glucose-induced downregulation of the hexose transport system in L8 myocytes. L8 myocytes were preconditioned with 2 mM glucose, washed and incubated with 2 mM dGlc. After 30 min a portion of the cells were washed again and incubated with 20 mM xylose, ribose, arabinose or lyxose. Cells were subjected to the dGlc uptake assay at various time points. As shown in FIG. 8, D-xylose was better than any of the other pentoses to reverse 2-deoxy-D-glucose-induced downregulation of the hexose transport system in L8 myocytes.

Some experiments with isolated rat soleus muscles were performed, in order to exclude cell-line specific effects, and to assess the physiologic relevance of the findings of the present invention. The results of a representative experiment are shown in FIG. 9. Soleus muscles were isolated from Sabra male albino rats and incubated for 3 hr with 20 mM glucose in the absence or the presence of 20 mM xylose. The muscles were washed and subjected to dGlc uptake assay without or with insulin (500 nM). FIG. 9 shows that D-xylose increased the rate of dGlc uptake by 42%.

In summary, the inventors have unexpectedly found that D-xylose increases the rate of glucose transport in skeletal muscle cells in a non-insulin dependent manner. D-xylose enters the cells and stimulates rapidly and markedly the glucose transport system. This effect of D-xylose is dose- and time-dependent. It induced upregulation of hexose transport in L8 and C2 myocytes, in L6 myotubes in culture and in isolated rat soleus muscles. These findings indicate that D-xylose can be developed as an antihyperglycemic agent, and/or may serve as a prototype molecule for the development of new antihyperglycemic agents by virtue of the potential ability to reverse the downregulatory effect of hyperglycemia.

EXAMPLE 2

Structure/Activity Studies of D-Xylose

D-xylose was active at high concentrations, and the half-life of D-xylose as measured in rats is short (30-60 min). These findings led to the working hypothesis that D-xylose may serve as a prototype molecule for the development of new antihyperglycemic agents by virtue of the potential ability to reverse the downregulatory effect of hyperglycemia. The inventors have therefore undertaken to produce xylose derivatives that are active at low concentrations with a long half-life and a high efficacy. Thus, chemical modifications were introduced in the xylose molecule to assess whether these modifications enhance and prolong its biological effect. To achieve this goal the inventors studied the structure/activity relationship of xylose and synthesized prototype derivatives and demonstrate herein that these derivatives are active at low concentrations with long half-life and high efficacy.

There are five carbon atoms in xylose available for chemical modifications. Each of these atoms was methylated by modifications of published chemical procedures [Bollenback, G. N. (1963) In Methods in carbohydrate chemistry, vol. 2 (Whistler, R. L. and Wolfrom, M. L., eds.), pp. 326-331, Academic Press, New York; Bowering, W. and Timel, T. (1958) *Can. J. Chem.* 36, 283-285; Levine, P. and Raymomd, A. (1933) *J. Biol. Chem.* 102, 331-344; Takeo, K. (1992) *Carbohyd. Res.* 224, 311-318]. All compounds were purified by HPLC and their structure verified by NMR spectroscopy. Table 1 shows results of screening assays of these derivatives, which were added for 2-48 hr to 3T3-L1 adipocytes and L6 myotubes that were pre-exposed to 20 mM glucose. At the end of the incubation period the cells were taken for a standard [$^3$H]-2-deoxy-D-glucose uptake assay in the absence or the presence of 500 nM insulin (30 min exposure prior to the uptake assay).

TABLE 1

| TEST COMPOUND | HEXOSE UPTAKE (Percent of Control) | |
|---|---|---|
| | Without Insulin | With Insulin |
| Control cells | 1.26 ± 0.10 (100%) | 4.20 ± 0.44 (100%) |
| D-xylose | 189 ± 4 | 158 ± 9 |
| 1-O-methyl xylopyranoside (1-O-methyl D-xylose) | 154 ± 4 | 156 ± 24 |
| 2-O-methyl xylopyranose (2-O-methyl D-xylose) | 63 ± 7 | 73 ± 15 |
| 3-O-methyl xylopyranose (3-O-methyl D-xylose) | 201 ± 30 | 159 ± 7 |
| 4-O-methyl xylopyranose (4-O-methyl D-xylose) | 72 ± 112 | 111 ± 2 |
| 5-O-methyl xylofuranose (5-O-methyl-D-xylose) | 70 ± 5 | 53 ± 22 |
| 1,3-O-dimethyl xylopyranoside (1,3-O-dimethyl D-xylose) | 267 ± 57 | 174 ± 28 |
| 1,2,3,4-O-tetramethyl xylopyranoside (1,2,3,4-O-tetramethyl D-xylose) | 95 ± 7 | 104 ± 8 |
| 2,3,4-O-trimethyl xylopyranose (2,3,4-O-trimethyl D-xylose) | 105 ± 9 | 94 ± 12 |

3T3-L1 adipocytes and L6 myotubes were maintained for 24 hr at 20 mM glucose. Test compounds were added (0.1-20.0 mM) and the cells were incubated further for 2-45 hr. At the end of the incubation periods the cells were washed and taken for a standard [$^3$H]2-deoxy-D-glucose (dGlc) uptake assay. Uptake values (given for control cells) are in nmol dGlc/mg protein/min. Mean±SEM (n=3-6).

These results show that carbon 2, 4 and 5 in D-xylose are not only critical for xylose action but their methylation causes downregulation of the hexose transport system in insulin-sensitive cells. Tri- and tetramethylation at positions 2, 3, 4 and 1, 2, 3, 4 produced inactive xylose derivatives. Of a major importance is the observation that mono- and dimnethylation at positions 1 and/or 3 augments the hexose transport system in 3T3-L1 adipocytes and L6 skeletal muscle myotubes (data not shown for the latter). It is important to emphasize that the hexose transport-stimulatory effect of these derivatives is insulin-independent, since they augmented the transport system both in the absence and presence of insulin.

These findings led to two strategies in developing new xylose derivatives: (A) Preparation of other 1-, 3- and 1,3-xylose derivatives with varying-length alkyl substituents. (B) Preparation of hydrophobic xylose derivatives at the critical positions with readily dissociating groups (spontaneous and enzyme-catalyzed).

Preparation of Biologically Active Novel D-xylose Derivatives

The inventors have prepared ethyl- and propyl-D-xylose derivatives. In addition, the inventors have also modified the structure of xylose by ketalyzation on the critical positions. Since D-xylose contains adjacent hydroxyl groups their ketalyzation was performed by available chemical procedures [Curtis, G. and Jones, K. (1960) Can. J. Chem. 38, 1305-1315, Ferrier, R. and Hatton, R. (1967) Carbohyd. Res. 5, 132-139]. This derivatization can increase the lipid solubility of the molecule, may prolong its half-life and facilitate its diffusional entry into target cells.

Both 3-O-ethyl xylose and 3-O-propyl xylose have never been synthesized and thus are novel compounds. Their synthesis followed the general principles described above for alkyl derivatization of xylose. The preparation of the PEG [methoxypoly(ethyleneglycol)-2000]-derivatives [di-4-(1-O-methyl-xylopyranoside)-phosphoryl-PEG-O-methyl] followed the procedures described by [Seeberger, P. and Caruthers, M. (1995) Tetrahedron Lett. 36, 695-698; Zalipsky, S. (1995) Bioconjug. Chem. 6, 150-165]. The synthesis of EH-3 (2,4:3,5-Di-O-benzylidene-D-xylose-dimethylacetal) and EH-36 (2,4:3,5 di-O-benzylidene-D-xylose-diethyl-dithioacetal) was based on procedures described by Ferrier and Horton (1967) and Curtis and Jones (1960). All compounds were HPLC-purified and their structure verified by NMR spectroscopy.

Table 2 summarizes in vitro results obtained with some of these newly synthesized xylose derivatives.

TABLE 2

| TEST COMPOUND | $EC_{50}$ | $EC_{max}$ | Fold Increase of Glucose Uptake |
|---|---|---|---|
| D-Xylose | 12 mM | 20 mM | ~2.0 |
| 1-O-methyl D-xylose | 6 mM | 10 mM | 1.5 |
| 3-O-methyl D-xylose | 2 mM | 4 mM | 2.0 |
| 1,3-O-methyl D-xylose | 2 mM | 4 mM | 3.0 |
| *3-O-ethyl D-xylose | 1.3 mM | 4 mM | 2.3 |
| *3-O-propyl D-xylose | 3 mM | 4.5 mM | 2.6 |
| *1-O-methyl D-xylose-PEG | 300 µM | 600 µM | 1.9 |
| EH-3 | 125 µM | 300 µM | 1.7 |
| EH-36 | 2 µM | 10 µM | 2.0 |

EH-3: 2,4:3,5-di-O-benzylidene-D-xylose-dimethylacetal
EH-36: 2,4:3,5 di-O-benzylidene-D-xylose-diethyl-dithioacetal;
EC = Effective concentration
*denotes novel D-xylose alkyl derivatives.

These data show that (I) methyl, ethyl and propyl ether substitutions at position 3 and methyl ether substitution at position 1 increase the potency of the compounds. (II) The potency of alkyl-xylose derivative is increased 30-fold when it is coupled to PEG. (III) The ketal derivative EH-36 was active at a µM range (2000-fold more potent than D-xylose), thus satisfying the criterion for a more potent compound. (IV) Maximal stimulatory effects of the alkyl-derivatives, the PEG-derivatives and EH-36 were obtained within 8-16, 24 and 48 h, respectively. The slow onset of action (24-48 hr) of EH-36 may reflect its accumulation in cells and the dissociation and release of the active moiety.

The inventors also tested the duration of action of these compounds after being washed from cell cultures. All compounds with alkyl substitutions at position 1 and/or 3 remained active for at least 2-4 hr following their removal. This is a substantial improvement to xylose whose activity is lost within 10-20 min after being removed. Moreover, the hexose-transport-augmenting activity of EH-101 (1,3-O-dimethyl xylopyranoside) and EH-114 (3-O-propyl-D-xylose) lasted 24 hr following removal from the culture media.

GLUT-1 and GLUT-4 mediate glucose entry into L6 myotubes. It is established that GLUT-4 is translocated effectively and rapidly to the plasma membrane upon insulin treatment. The inventors looked at the effect of 3-O-propyl-D-xylose EH-114) and 1,3-O-dimethylxylopyranoside (EH-101) on the total cell content and plasma membrane abundance of these transporters in the absence or presence of insulin. L6 myotubes were maintained at 5.0 or 23.0 mM glucose for 48 hr and EH-114 and EH-101 were present during the last 24 hr. The cells were then taken for the standard [$^3$H]-2-deoxy-D-glucose uptake assay and for the biotinylation procedure for determining the amount of GLUT-1 and GLUT-4 in the plasma membrane. High glucose levels decreased the hexose transport rate by ~50%. Insulin augmented the transport nearly 2-fold in both cases. EH-114 and EH-101 increased the transport rate 2-3-fold in the absence of insulin. Together with insulin the uptake rate was increased nearly 3-fold.

FIG. 10 presents the western blots showing the results of such a representative experiment. Under hyperglycemic conditions the total cell content of GLUT-4 was reduced as well as its plasma membrane abundance [lanes 1 & 2 for Total cell content and PM (plasma membrane) fractions]. Insulin (500 nM) induced, as expected, translocation of GLUT-4 to the plasma membrane under both glycemic conditions (lanes 7 & 8). The important findings of this experiment are: 3-O-propyl-D-xylose and 1,3-O-dimethylxylo-pyranoside induced significant translocation of GLUT-4 to the plasma membrane of the cells in the absence of insulin. This translocation activity was more effective than the effect of insulin per se (compare lanes 3 & 5 to lanes 4 & 6). When added together with insulin, the combined effect of these two compounds and insulin seems additive [compare lanes 3 & 5 to lanes 4 & 6 (PM blot)]. Similar blots with anti GLUT-1 antibody revealed no effect of insulin or these xylose derivatives (data not shown). This is the first evidence that xylose derivatives augment glucose transport by augmenting specifically the translocation of GLUT-4, but not GLUT-1, to the plasma membrane in the absence of insulin. Thus, they mimic the translocation effect of insulin, but unlike insulin this translocation mechanism requires several hours compared to the rapid effect of insulin (minutes).

Another conclusion from these experiments is the possible effects of EH-101 (1,3-O-dimethyl xylopyranoside) and EH-114 (3-O-propyl-D-xylose) on the total content of GLUT-4. Both seem to have increased the total content of the transporter in L6 cells exposed to 23.0 mM glucose (compare lanes 3 and 5 to 2, for Total GLUT-4). This raises the possibility that this effect is at the transcription level of GLUT-4 gene and/or post-transcriptional regulation by stabilization of the GLUT-4 mRNA and/or protein.

The inventors also tested the hypothesis that the active D-xylose derivatives augment the hexose transport capacity in L6 myotubes by translocating GLUT-4 to the plasma membrane not via the common insulin-regulated pathway. For this experiment, a selective inhibitor of the enzyme PI3-kinase, LY-249002, which is a key enzyme in the cellular transduction mechanism of insulin, was utilized. FIG. 11A shows that this inhibitor eliminated the stimulatory effect of insulin but failed to affect the augmenting effect of D-xylose and its derivatives EH-101 and EH-114. These findings indicate that the mechanism of action of the alkylated D-xylose derivatives differ significantly from that of insulin and that it does not employ the initial events in the insulin-dependent cascade that ultimately induce translocation of GLUT-4 from an intracellular vesicular pool to the plasma membrane of the cells. These findings also agree well with the longer onset of action of these derivatives as compared to the rapid action of insulin. Similar results were obtained when LY-249002 was present together with the derivatives throughout the entire incubation period.

Another experiment using EH-40 (2,4benzylidene-D-xylose-diethyl-dithioacetal) indicated that this PI3K inhibitor abolished EH-40-dependent augmentation of hexose transport (data not shown). These data suggest that the alkyl derivatives utilize a cellular mechanism that is not dependent on PI3K activation, while the mechanism of action of the aromatic derivatives may involve PI3K activation.

In order to test whether xylose derivative activate insulin transduction elements downstream of PI3K, the inventors tested the state of PKB phosphorylation, as shown in FIG. 11B. Insulin, as expected, induced prominent, but transient phosphorylation of PKB. D-xylose and EH-114 failed to induce significant phosphorylation of PKB. However, EH-40 induced a time-dependent and sustained phosphorylation of PKB, which parallels the EH-40-dependent stimulation of hexose transport in these myotubes.

In addition, a new derivative—EH-169 (3-O-methyl-2,4-O-benzylidene-D-xylose-diethyl-dithioacetal—FIG. 16), which contains both O-methyl substitution at position 3 and benzylidene substitution at position 2 and 4, was synthesized. This 'chimeric' compound increased [$^3$H]-2-deoxy-D-glucose uptake in L6 myotubes 1.8 and 2-fold at 60 and 120 µM.

In summary, the present invention for the first time discloses the design and synthesis of pentose derivatives, and in particular D-xylose derivatives, that are active at low concentrations with long half-life and high efficacy. The results show that alkyl substitution at positions 1 and/or 3 increases the hexose transport augmenting effect of xylose in cultured cells in an insulin-independent manner. This effect lasts after the removal of the compounds from the cell cultures. These compounds, like xylose, were active at mM range, yet they were at least 2-5-fold more potent than xylose. In addition, PEG-derivatization of 1-O-methyl xylose increases 30-fold the potency of 1-O-methyl xylose. Ketalyzation of xylose produces very potent compounds (2000-fold more active than xylose). These compounds, and especially EH-36 are active at a µM range and their action is preserved after washing them from the cell. Finally, it was shown that xylose derivatives induce translocation of GLUT-4 to the plasma membrane of insulin-sensitive cells without affecting GLUT-1 cellular localization. There is some evidence that these compounds also increase the total cell content of GLUT-4.

EXAMPLE 3

In-Vivo Studies in Diabetic Mice

EH-36 was tested for its potential anti-hyperglycemic activity in an animal model of diabetes. Male C57/black mice were made diabetic by daily i.p. injections of streptozotocin (50 mg/Kg) for 5 days. After 10 days the fasting blood glucose of these mice was above 300 mg/dL as compared to 80-130 mg/dL of control mice. Unlike a single and high dose injection of streptozotocin, which produces an animal model for Type 1 diabetes, the repeated low-dose injections produce a model that more closely resembles Type 2 diabetes. (Fraser, R. B., Rowden, G., Colp, P, And Wright, J. R. Jr.: Immunophenotyping of insulitis in control and essential fatty aid deficient mice treated with multiple low-dose streptozotocin. *Diabetologia*, 40:1263-1268, 1997).

EH-36 was dissolved in sesame oil (4 mg/ml) and injected into Streptozotocin-diabetic mice (s.c. 400 µg, twice a day at 08 and 18 hrs). Blood was withdrawn from the tip of the tails and glucose levels were measured with a glucometer.

FIG. 12 depicts the results obtained from these animals. These data indicate that EH-36 has a blood-glucose-lowering potential. Neither EH-36 nor the vehicle changed significantly the blood glucose level of non-diabetic mice. This is the first evidence that EH-36 lowers blood glucose in hyperglycemic animal models. The data obtained from the treated rats are presented in bold lines FIG. 13 shows representative results obtained in streptozotocin-diabetic C57 black mice. Diabetic C57 black mice were treated with EH-36 (full symbols) or the vehicle (sesame oil, empty symbols) twice a day by s.c. injections and their blood glucose levels determined as described above. The treated animals are represented in bold lines. While all the control mice that received oil injections remained hyperglycemic, the EH-36-treated mice reduced their blood glucose level to the normoglycemic range. Two of the treated animals reverted to the hyperglycemic state after a 2-3 day period of normo- or near normoglycemia. This phenomenon was observed in several animals. One possibility is that the aromatic substitutions within the EH-36 molecule may by themselves be inducers of specific cytochrome P450 isoenzymes in the liver, which may accelerate the metabolic elimination of the drug.

In another set of experiments similar diabetic mice were treated with the oil or EH-36 (1.5 mg, s.c. twice a day) for 9 days. On the morning of the $10^{th}$ day and following an overnight fast the mice were subjected to a glucose tolerance test (GTT). The mice received D-glucose by i.p. injections (2 gr/kg body weight). Blood glucose as monitored for 3 hr at 30 min intervals.

The area under the curve (AUC) of each GTT was calculated and is shown in FIG. 14. The average AUC values are 12.3±1.6 and 6.42±1.62 mg glucose/ml/hr (±SEM), for control and EH-36-treated mice, respectively. These results indicate that in most cases EH-36 improves glucose clearance by nearly 50% following a 9-day treatment.

Interestingly, when these animals were left untreated for four additional weeks after injecting oil or EH-36, all the control animals developed serious complications associated with diabetes (weight loss, excessive urination and lethargy) and some died. However, the EH-36 treated animals looked normal and healthy. Their blood glucose levels ranged between 250-350 mg/dL compared to greater than 600 mg/dL in oil-treated animals. The photographs shown in FIG. 15 are of an oil-treated mouse (left) and EH-36-treated mouse (right) three weeks after a course of 9-day injection protocol. While the control mice were lethargic and urinated massively, the EH-36-treated mice were alert and behaved and urinated normally.

These surprising results show that EH-36 has a long lasting effect that is apparent at least 3 weeks after treatment. This is not due to a retarded absorption of the drug, since when the mice were sacrificed and the injection area was examined, there was no evidence for oil or drug accumulation. Yet, due to the hydrophobic nature of EH-36 it is possible that it accumulated in adipose cells and fat depots, and was released continuously days after the last injection.

In summary, the results of these experiments demonstrate that EH-36 was active in vivo and reduced the blood glucose level of diabetic mice. A rebound effect under EH-36 treatment may be related to an accelerated clearance of the drug due to induction of hepatic microsomal enzymes. EH-36 has a long lasting effect in diabetic mice (at least 3 weeks after the last injection). This may be related to accumulation of the compound in fat depots and its slow release into the circulation.

EXAMPLE 4

Design and Synthesis of Additional Xylose Derivatives

Based upon the above results, the inventors have designed and synthesized compounds that combine the properties of EH-36 and of 1-O- and 3-O-alkyl substituted D-xylose or diethanethiol-xylose derivatives.

In order to initiate such a synthesis, 2,4-benzylidene-D-xylose-diethyl-dithioacetal (with a benzylidene substitution only at positions 2 and 4, leaving positions 3 and 5 free, EH-40) was prepared by the procedure described by Ferrier and Hatton (1967). The yield of EH-40 was ~30%, as determined by NMR spectroscopy. Next, EH-40 was extracted from the reaction mixture that contained 7 additional compounds by preparative layer chromatography (PLC), using a mobile phase of 98% ether and 2% methanol. The purity of the extracted compound was tested by NMR and melting point determination (140° C.). Apart from being the starting material for the synthesis of derivatives containing 1-O- or 3-O-substitutions (methyl, ethyl, propyl and piperidine), this compound (EH-40) is also tested in vitro and in vivo. Since it is less hydrophobic than EH-36 it may also be injected in animals at higher doses than EH-36.

Another hypothesis that was tested is that the starting compound D-xylose-diethyl-dithioacetal (EH-27) for the synthesis of EH-36 may have antioxidant properties due to release of the thiolalkyl moiety in the cells. The inventors also synthesized similar compounds (D-xylose with a thioalkyl substitution at position 1) but with longer alkyl moieties. The newly synthesized compounds are: D-xylose-diethyl-dithioacetal (EH-128), β-ethylthioxylo-pyranoside (EH-143) and β-laurylthioxylopyranoside (EH-146). In order to determine whether the thioalkyl moiety acts as an antioxidant when released in the cells, the inventors have synthesized two more xylose derivatives containing classical thio-antioxidants: di-N-acetylcysteinethioxyloside (EH-63) and di-cysteinethioxyloside (EH-64). The inventors further disclose the process of synthesizing a similar lipoic acid derivative. The thioalkyl moiety in the xylose molecule may confer antioxidant activity in addition to the effect of the xylose itself.

Chemical Syntheses of Additional Compounds

1. Preparation of alkyl, ketal and alkyl-ketal derivatives of xylose:

The new alkyl and ketal derivatives show improved pharmacodynamic parameters in comparison to xylose. Yet, the ketal derivatives are potent at a µM range while the alkyl derivatives are potent at a mM range. The ketal derivative EH-36, though active in vivo, is highly hydrophobic and has very limited solubility in most common organic solvents (e.g., DMSO, ethanol and oil). Therefore xylose derivatives alkylated (O-methyl O-propyl etc.) at position 1 and/or 3 in addition to ketal derivatization at position 2 and 4 with moieties that are less hydrophobic than the benzyl group of EH-36 (such as thiobenzaledene, carboxybenzaledene, aminobenzaledene and fatty acids of various length) may render compounds having improved solubility. Each successful drug may also be combined to PEG [methoxypoly(ethyleneglycol)-2000], a procedure common in pharmaceutical chemistry to increase drug absorption, potency and availability in vivo. Recently, the inventors have synthesized EH-40 (2,4-benzylidene-D-xylose-diethyl-dithioacetal) which serves as the parent compound for the synthesis of mixed 3-O-alkyl and acetal derivatives (3-O-methyl-2,4-benzyledene-D-xylopyranose, 3-O-ethyl-2,4-benzyledene-D-xylopyranose, 3-O-propyl-2,4-benzyledene-D-xylopyranose) and mixed 3-O-alkyl and diethanethiol-2,4-benzyledene derivatives (diethanethiol-3-O-methyl-2,4,-benzyledene-D-xyloside, diethanethiol-3-O-ethyl-2,4,-benzyledene-D-xyloside, diethanethiol-3-O-propyl-2,4,-benzyledene-D-xyloside).

Additional compounds are:

1.2. Alkyl Derivatives:

α,β-3-O-butyl-D-xylopyranose and α,β-3-O-isopropyl-D-xylopyranose may be synthesized using the procedures described above.

1.3. Dithioacetal-D-xyloside Derivatives:

Diethanethiol-2,4-3,5-dithiobenzyaledene-D-xyloside, diethanethiol-2,4-3,5-dicarboxybenzyaledene-D-xyloside, and diethanethiol-2,4-3,5-ditaminobenzyaledene-xyloside.

1.4. Mixed 3-O-alkyl and Acetal Derivatives:

3-O-methyl-,4-3,5-dithiobenzyaledene-D-xyloside, 3-O-ethyl-2,4-3,5-icarboxy-benzyaledene-D-xyloside, and 3-O-propyl-2,4-3,5-diaminobenzyaledene-D-xyloside. Similar butyl- and isopropyl-derivatives may be prepared if the respective alkyl substitutions will produce active compounds.

1.5. Mixed 1,3-O-dialkyl and Acetal Derivatives:

1,3-dimethyl-2,4-benzyledene-D-xylopyranoside, 1,3-dimethyl-2,4-carboxybenzyl-edene-D-xylopyranoside, 1,3-dimethyl-2,4-thiobenzyledene-D-xylopyranoside, 1,3-dimethyl-2,4-aminoenzyledene-D-xylopyranoside.

1.6. Mixed 3-O-alkyl and diethanethiol-2,4-benzyledene Derivatives:

Diethanethiol-3-O-methyl-2,4,-benzyledene-D-xyloside, diethanethiol-3-O-ethyl-2,4,-benzyledene-D-xyloside, diethanethiol-3-O-propyl-2,4-benzyledene-D-xyloside and all the respective thiocarboxy- and aminobenzaledene derivatives.

1.7. PEG Derivatives:

Each successful compound is combined with PEG [methoxy-poly-(ethyleneglycol)200] via phosphate bond or amide bond to produce compounds, such as polyethylglycomonomethylether(2000)-di-diethanethiol-3-O-propyl-2,4-benzaledene-D-xyloside-5P-triester.

1.8. Thioalkyl Derivatives:

Applicant's findings on the hexose transport augmenting activity of dipropanethioxyloside (EH-128), β-ethylthio-D-xylopyranoside (EH-143) but not βlaurylthio-D-xylopyranoside (EH-146) serve as the basis for synthesis of similar compounds with varying length thioalkyl moieties (4 to 10 carbon atoms). In addition, disclosed herein are the following thioalkyl-ketal chimeras: Dipropanethio-3-O-propyl-D-xylopyranoside, dibutanethio-3-O-propyl-D-xylopyranoside and dimercaptoethanol-3-O-propyl-D-xylopyranoside.

1.9. Non-aromatic EH-36-Like Compounds:

Since the aromatic benzylidene substitutions in EH-36 may act as inducers of hepatic microsomal enzymes that accelerate the clearance of the compound, the inventors proceeded to synthesize other ketal and acetal-D-xylose derivatives, with no aromatic structures, for instance, hexalidene, pentalidene and octalidene. The principle of their synthesis is similar to that of EH-36 but with hexa-, penta- or octaldehyde.

EXAMPLE 5

Methods and Procedures

Chemical Procedures:

All the procedures for new derivatives follow those described above for alkyl-ketal- and PEG-derivatives. All new compounds are purified by HPLC and/or Flash chromatography and analyzed by NMR spectroscopy. Other methods include: melting point determination, mass spectroscopy, IR spectroscopy and elementary analysis.

In vitro Studies:

Tissue Cultures:

Skeletal muscle cell and 3T3-L1 adipocyte cultures will be grown and maintained as described. (Coumas, J V., dos-Remedios, C. G.: Actin-binding proteins in mouse C2 myoblasts and myotubes: a combination of affinity chromatography and two-dimensional gel electrophoresis. Electrophoresis, 19:826-833, 1998; Gosset, L-A., Shang, W., Olson, E. N.: Dexamethasone-dependent inhibition of differentiation of C2 myoblasts bearing steroid-inducible N-ras oncogene. J. Cell. Biol. 106:2127-2137, 1988; Alogh, S., Naus, C. C., Merrifield, P. A.: Expression of gap junction in cultures rat L6 cells during myogenesis. Dev. Biol. 155:351-360, 1993; Rudich, A., Kozlovsky, N., Potashnik, R., Bashan, N. Oxidant stress reduces insulin responsiveness in 3T3-L1 adipocytes. Am. J. Physiol. 272:E935-E940, 1997.

Hexose Uptake Assay:

Uptake assay of the tritiated glucose analogue, 2-deoxy-D-glucose, is routinely performed as described in [Sasson, S. and Cerasi, E. (1986) *J. Biol. Chem.* 261, 16827-16833].

Cell Surface Biotinylation and the Determination of Cell Surface GLUT-1 and GLUT-4:

Surface biotinylation of the cells was performed as previously described [Sasson et al (1997), Diabetologia, 40, 30-398].

All new compounds are screened and tested first in various insulin-sensitive cell cultures used routinely in the laboratory (skeletal muscle and adipose cell lines). In addition these drugs were tested in non-insulin-sensitive cells such as primary cultures of bovine and porcine vascular endothelial and smooth muscle cells. Active compounds were tested ex-vivo on isolated rat soleus muscles. All cell cultures and tissues were maintained under hyperglycemic condition prior to the addition of the test compounds. Dose-response and time-course experiments determine which of the derivatives are subsequently tested in animal models. For each potent compound the total cell content and plasma membrane abundance of GLUT-1 and GLUT-4 was determined, as described above. The same biotinylation technique was employed to determine the total and plasma membrane content of both transporters in isolated mouse or rat soleus muscles treated with potent compounds.

In vivo Studies

Animal Models

The inventors used streptozotodin diabetic C57 black mice, rats, NOD mice and *Psammomys obesus* to test the newly synthesized derivatives.

In all animal models (and their appropriate controls) the xylose derivatives are administered daily by injection (i.p. or s.c.) according to the type of product as mixed in oil/water or oil or by a cannula. The evolution of the diabetic syndrome is followed by frequent blood glucose measurements and occasional sampling for plasma insulin. In successful experiments, the soleus muscle and/or epididymal fat tissue are removed for ex vivo testing of glucose transport. Furthermore, pancreatic tissue is removed to ascertain to what extent our treatments permit replenishment of the endogenous insulin stores, and reversal of the β-cell apoptosis observed in prolonged diabetes in *Psammomys*. In selected animals, the in vivo glucose/insulin metabolism is tested by intraperitoneal glucose challenges.

Drug Administration:

Rats and mice were treated repeatedly with low dose streptozotocin, as described above, and used when blood glucose reached levels higher than 300 mg/dL. These and the various animal models described above as well as the non-diabetic control animals were treated with active xylose derivatives. Each compound is dissolved in an appropriate solvent (saline, DMSO, oil, etc.) and injected s.c. or i.p. Active compounds were administered p.o. as well. Blood glucose was measured as described above. Control animals were treated similarly with the vehicles and drugs.

Hexose Uptake Assay in Isolated Skeletal Muscle and Fat Tissue:

The procedure follows that described before in [Sasson et al (1987), *Diabetes* 36, 1041-46].

Pharmacokinetic Studies

In preparation for these experiments we have determined the following: 1. The spectra analysis of EH-36 indicated maximum absorbance at 272 nm. 2. EH-36 was added to freshly isolated rat serum. Following extraction and HPLC analysis the obtained profile was compared to a HPLC profile of serum extracts prepared from untreated rat. A distinct peak of EH-36 was identified. It was eluted at 9.6 min, similar the elution time of the pure EH-36, which was analyzed by HPLC under the same conditions.

Extract aliquots (30 µl) were analyzed by reverse phase HPLC in a 150×4.6 mm, 3µ ODS Hypersil® column (Thermohypersil-Keystone, Bellfonte, Pa.) connected to an L-4200 UV-Vis detector (272 nm). Elution was at a flow rate of 1.5 ml/min with water and acetonitrile gradient: the initial solvent mixture was 30% water:70% acetonitrile:. A convex gradient over 20 min then followed to 100% acetonitrile.

The pharmacokinetic parameters of EH-36 were determined by the following procedure. Rats (3 per group per time point) were anesthetized and their blood collected from the portal vein. The serum was separated and extracted with chloroform. The extract was dried and redissolved in a small volume of chloroform and separated by HPLC and identified by UV absorption. The animals were treated with 16 mg/day (in sesame oil, s.c.) for 3 days. On the fourth day the animals were sacrificed and serum was isolated, extracted and separated by HPLC. There was a distinct peak of EH-36 corresponding to 1.01 mg/ml EH-36. To verify that this peak corresponds to EH-36 a known quantity of this compound was added to a serum sample taken from the EH-36-treated rats. Following extraction and HPLC analysis the only peak that was intensified was that corresponding to EH-36. Taken together, these preliminary finding constitute a method for determining the half-life of EH-36 and other pharmacokinetic parameters in rodents and other animal models.

This procedure used to determine the pharmacokinetic parameters of EH-36 and other compounds in normal and diabetic mice and rats. HPLC conditions are determined individually for each compound.

Biochemical Profiling

In addition to blood glucose determination, the inventors also determined the plasma insulin levels, ketone bodies and lipid profile. These determinations are done routinely for each in vivo potent drug. These tests are also conducted on animals three weeks after the treatment with EH-36, since, as described above, it was found that these mice survived their diabetic condition unlike the control, oil-treated mice.

It will be appreciated by a person skilled in the art that the present invention is not limited by what has been particularly shown and described hereinabove. Rather, the scope of the invention is defined by the claims that follow.

What is claimed is:

1. A pentose derivative represented by the structure of formula V:

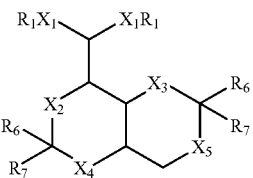

wherein
$X_1$ is O or S;
$X_2$, $X_3$, $X_4$ and $X_5$ are each S;
$R_1$ is independently at each occurrence hydrogen, an amino acid containing a thiol or hydroxyl group in its sidechain, or an alkyl, allyl, phenyl or acyl group; and
$R_6$ and $R_7$ are independently of each other a hydrogen, an alkyl or phenyl,
or a methoxy-polyethyleneglycol (PEG) derivative, a pharmaceutically acceptable salt, or hydrate thereof.

2. A pharmaceutical composition comprising the pentose derivative of claim 1, and a pharmaceutically acceptable carrier or excipient.

3. The composition according to claim 2, wherein the composition is in a form selected from the group consisting of a tablet, a pellet, a capsule, a suspension, an emulsion, a gel, a cream, a depot, a suppository, an intra-vaginal ring, and a parenteral formulation.

4. A method of treating diabetes in a subject, comprising the step of administering to the subject a pentose derivative according to claim 1, in an amount effective to lower blood glucose levels in the subject, thereby treating diabetes in the subject.

5. A method of treating hyperglycemia or a complication of hyperglycemia in a subject, comprising the step of administering to said subject a pentose derivative according to claim 1, in an amount effective to lower blood glucose levels in said subject, thereby treating hyperglycemia or a complication of hyperglycemia in the subject.

6. A method for treating daily blood glucose fluctuations in a subject or improving the ability of a subject to metabolize glucose, the method comprising administering to a subject in need of such treatment a pentose derivative according to claim 1 in an amount effective to treat daily blood glucose fluctuations in the subject or improve the ability of the subject to metabolize glucose.

7. A pentose derivative represented by the structure of formula VII:

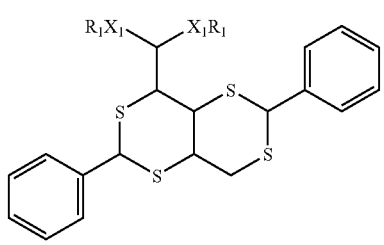

wherein $X_1$ is O or S; and $R_1$ is independently at each occurrence hydrogen, an amino acid containing a thiol or hydroxyl group in its side-chain, or an alkyl, allyl, phenyl or acyl group,
or a methoxy-polyethyleneglycol (PEG) derivative, a pharmaceutically acceptable salt, or hydrate thereof.

8. A pharmaceutical composition comprising the pentose derivative of claim 7, and a pharmaceutically acceptable carrier or excipient.

9. The composition according to claim 8, wherein the composition is in a form selected from the group consisting of a tablet, a pellet, a capsule, a suspension, an emulsion, a gel, a cream, a depot, a suppository, an intra-vaginal ring, and a parenteral formulation.

10. A method of treating diabetes in a subject, comprising the step of administering to the subject a pentose derivative according to claim 7, in an amount effective to lower blood glucose levels in the subject, thereby treating diabetes in the subject.

11. A method of treating hyperglycemia or a complication of hyperglycemia in a subject, comprising the step of administering to said subject a composition according to claim 7, in an amount effective to lower blood glucose levels in said subject, thereby treating hyperglycemia or a complication of hyperglycemia in the subject.

12. A method for treating daily blood glucose fluctuations in a subject or improving the ability of a subject to metabolize glucose, the method comprising administering to a subject in need of such treatment a pharmaceutical composition according to claim 7 in an amount effective to treat daily blood glucose fluctuations in the subject or improve the ability of the subject to metabolize glucose.

13. A pharmaceutical composition comprising as an active ingredient a pentose derivative represented by any one of formulae I-III:

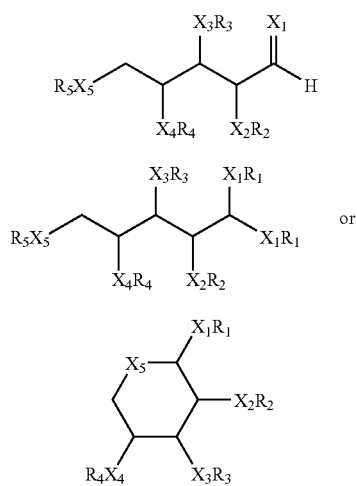

wherein
$X_1$ and $X_3$ are O or S;
$R_1$ and $R_3$ are independently of each other methyl, ethyl, propyl or isopropyl;
$X_2$, $X_4$ and $X_5$ are independently of each other O, S, or NH;
$R_2$, $R_4$ and $R_5$ are independently of each other hydrogen or an alkyl, allyl, or phenyl,
or any one or more of $R_1$ together with $R_2$, $R_1$ together with $R_3$, $R_2$ together with $R_3$, $R_2$ together with $R_4$, $R_3$ together with $R_4$, $R_3$ together with $R_5$, or $R_4$ together with $R_5$, represent a $CR_6R_7$ group wherein $R_6$ and $R_7$ are independently of each other a hydrogen, an alkyl or phenyl, provided that when $X_1$-$X_5$ are oxygen and $R_2$, $R_4$ and $R_5$ are hydrogen, at least one of $R_1$ and $R_3$ is other than methyl;
or a methoxy-polyethyleneglycol (PEG) derivative, a pharmaceutically acceptable salt, or hydrate thereof; and
at least one pharmaceutically acceptable carrier or excipient selected from the group consisting of a binder, a disintegrating agent, a detergent, a surfactant, a viscosity increasing agent, an emulsifier and a lubricant.

14. The composition of claim 13, wherein the pentose derivative is a xylose, ribose, arabinose, or lyxose derivative.

15. The composition according to claim 13, wherein the composition is in a form selected from the group consisting of a tablet, a pellet, a capsule, a suspension, an emulsion, a gel, a cream, a depot, a suppository, an intra-vaginal ring, and a parenteral formulation.

16. A method of treating diabetes in a subject, comprising the step of administering to the subject a composition according to claim 13 in an amount effective to lower blood glucose levels in the subject, thereby treating diabetes in the subject.

17. A method of treating hyperglycemia or a complication of hyperglycemia in a subject, comprising the step of administering to said subject a composition according to claim 13, in an amount effective to lower blood glucose levels in said subject, thereby treating hyperglycemia or a complication of hyperglycemia in the subject.

18. A method for treating daily blood glucose fluctuations in a subject or improving the ability of a subject to metabolize glucose, the method comprising administering to a subject in need of such treatment a composition according to claim 13 in an amount effective to treat daily blood glucose fluctuations in the subject or improve the ability of the subject to metabolize glucose.

19. A pharmaceutical composition comprising as an active ingredient a pentose derivative represented by any one of formulae I-III:

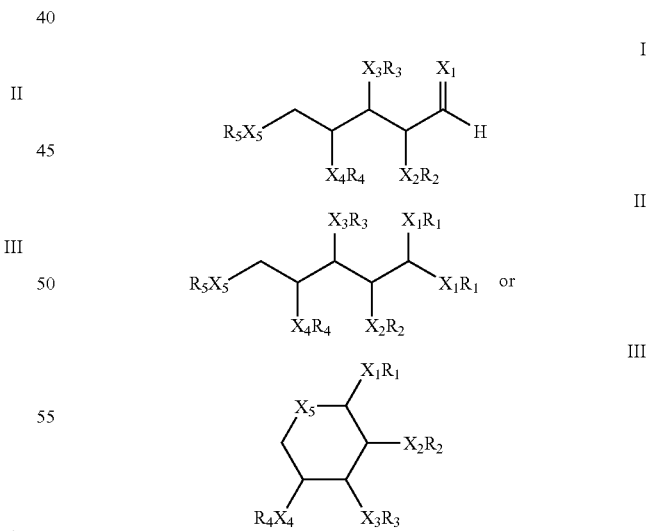

wherein
$X_1$ and $X_3$ are O or S;
$X_2$, $X_4$ and $X_5$ are independently of each other O, S, or NH;
$R_1$ and $R_3$ are independently of each other hydrogen, an amino acid containing a thiol or hydroxyl group in its side-chain, or an alkyl, allyl, phenyl or acyl group;

R$_2$, R$_4$ and R$_5$ are independently of each other hydrogen or an alkyl, allyl, or phenyl, wherein at least one of R$_1$ together with R$_2$, R$_1$ together with R$_3$, R$_2$ together with R$_3$, R$_2$ together with R$_4$, R$_3$ together with R$_4$, R$_3$ together with R$_5$, or R$_4$ together with R$_5$, represent a CR$_6$R$_7$ group wherein R$_6$ and R$_7$ are independently of each other a hydrogen, an alkyl or phenyl, or a methoxy-polyethyleneglycol (PEG) derivative, a pharmaceutically acceptable salt, or hydrate thereof; and at least one pharmaceutically acceptable carrier or excipient selected from the group consisting of a binder, a disintegrating agent, a detergent, a surfactant, a viscosity increasing agent, an emulsifier and a lubricant.

20. The composition of claim 19, wherein the pentose derivative is a xylose, ribose, arabinose, or lyxose derivative.

21. The composition according to claim 19, wherein the active ingredient is represented by at least one of the structures of formulae IV or V:

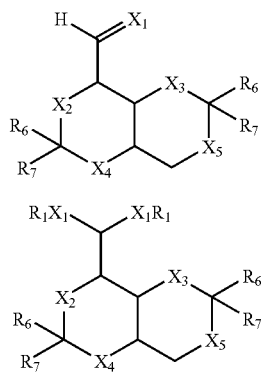

wherein X$_1$- X$_5$, R$_1$, R$_6$ and R$_7$ are as defined-in claim 19.

22. The composition according to claim 19 wherein the active ingredient is represented by at least one of the structures of formulae VI or VII:

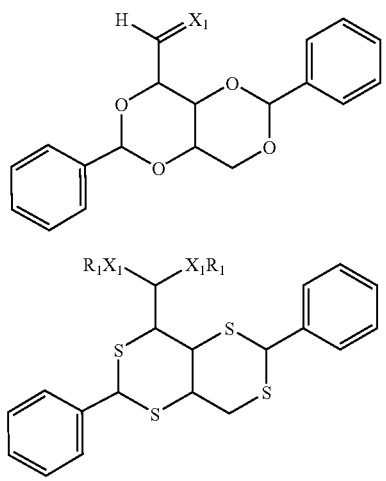

wherein X$_1$ and R$_1$ are as defined in claim 19.

23. The composition according to claim 19, wherein the composition is in a form selected from the group consisting of a tablet, a pellet, a capsule, a suspension, an emulsion, a gel, a cream, a depot, a suppository, an intra-vaginal ring, and a parenteral formulation.

24. A method of treating diabetes in a subject, comprising the step of administering to the subject a pharmaceutical composition according to claim 19 in an amount effective to lower blood glucose levels in the subject, thereby treating diabetes in the subject.

25. A method of treating hyperglycemia or a complication of hyperglycemia in a subject, comprising the step of administering to said subject a pharmaceutical composition according to claim 19, in an amount effective to lower blood glucose levels in said subject, thereby treating hyperglycemia or a complication of hyperglycemia in the subject.

26. A method for treating daily blood glucose fluctuations in a subject or improving the ability of a subject to metabolize glucose, the method comprising administering to a subject in need of such treatment a composition according to claim 19 in an amount effective to treat daily blood glucose fluctuations in the subject or improve the ability of the subject to metabolize glucose.

27. A pharmaceutical composition comprising an active ingredient is selected from the group consisting of
3-O-ethyl-D-xylose;
3-O-propyl-D-xylose;
1-O-methyl-D-xylose PEG;
2,4:3,5-di-O-benzylidene-D-xylose-dimethylacetal;
2,4:3,5-di-O-benzylidene-D-xylose-diethyl-dithioacetal;
3-O-ethyl-2,4-O-benzylidene-D-xylose-diethyl-dithioacetal;
propyl-thio-β-xylopyranoside;
ethyl-thio-β-xylopyralloside;
lauryl-thio-β-xylopyranoside;
D-xylose-di-N-acetylcysteine-dithioacetal;
D-xylose-di-cysteine-dithioacetal;
D-xylose-diethyl-dithioacetal;
D-xylose-dipropyl-dithioacetal;
1,3-O-dimethylxylopyranoside;
2,4-benzylidene-D-xylose-diethyl-dithioacetal;
3-O-methyl-2,4-O-benzylidene-D-xylose-diethyl-dithioacetal;
3-O-propyl-2,4-O-benzylidene-D-xylose-diethyl-dithioacetal;
3-O-ethyl-5-O-benzoyl-D-xylose-diethyl-dithioacetal;
3-O-propyl-1,2-benzylidene-D-xylose; and
3-O-propyl-2,4-benzylidene-D-xylose;
and a pharmaceutically acceptable carrier or excipient.

28. The composition according to claim 27, wherein the composition is in a form selected from the group consisting of a tablet, a pellet, a capsule, a suspension, an emulsion, a gel, a cream, a depot, a suppository, an intra-vaginal ring, and a parenteral formulation.

29. A method of treating diabetes in a subject, comprising the step of administering to the subject a pharmaceutical composition according to claim 27 in an amount effective to lower blood glucose levels in the subject, thereby treating diabetes in the subject.

30. A method of treating hyperglycemia or a complication of hyperglycemia in a subject, comprising the step of administering to said subject a composition according to claim 27, in an amount effective to lower blood glucose levels in said subject, thereby treating hyperglycemia or a complication of hyperglycemia in the subject.

31. A method for treating daily blood glucose fluctuations in a subject or improving the ability of a subject to metabolize glucose, the method comprising administering to a subject in need of such treatment a composition according to claim 27 in an amount effective to treat daily blood glucose fluctuations in the subject or improve the ability of the subject to metabolize glucose.

32. A method for treating daily blood glucose fluctuations in a subject or improving the ability of a subject to metabolize glucose, the method comprising administering to a subject in need of such treatment a pentose derivative represented by at least one of the structures of formulae I-III in an amount effective to treat daily blood glucose fluctuations in the subject or improve the ability of the subject to metabolize glucose

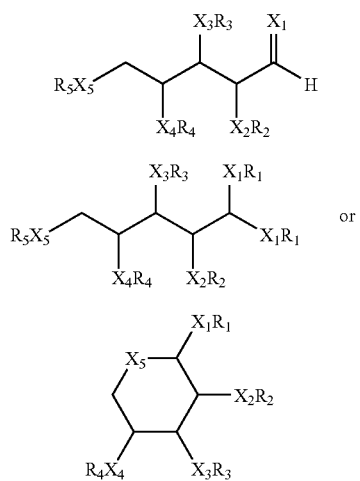

wherein
(a) for the compounds of formula I or II:
$X_1$ and $X_3$ are O or S;
$R_1$ and $R_3$ are independently of each other methyl, ethyl, propyl or isopropyl;
$X_2$, $X_4$ and $X_5$ are independently of each other O, S, or NH;
$R_2$, $R_4$ and $R_5$ are independently of each other hydrogen or an alkyl, allyl, phenyl or acyl group,
or at least one of $R_1$ together with $R_2$, $R_1$ together with $R_3$, $R_2$ together with $R_3$, $R_2$ together with $R_4$, $R_3$ together with $R_4$, $R_3$ together with $R_5$, or $R_4$ together with $R_5$, represent a $CR_6R_7$ group wherein $R_6$ and $R_7$ are independently of each other a hydrogen, an alkyl or phenyl, provided that $R_2$ together with $R_4$ and $R_3$ together with $R_5$ do not simultaneously represent CH-phenyl;
and wherein
(b) for the compound of formula III:
$X_1$ and $X_5$ are each S,
$R_1$ and $R_3$ are independently of each other methyl, ethyl, propyl or isopropyl;
$X_2$, $X_3$ and $X_4$ are independently of each other O or S;
$R_2$ is alkyl, allyl or phenyl;
$R_4$ is hydrogen or an alkyl, allyl, phenyl or acyl group;
or at least one of $R_1$ together with $R_2$, $R_1$ together with $R_3$, $R_2$ together with $R_3$, $R_2$ together with $R_4$, $R_3$ together with $R_4$, $R_3$ together with $R_5$, or $R_4$ together with $R_5$, represent a $CR_6R_7$ group wherein $R_6$ and $R_7$ are independently of each other a hydrogen, an alkyl or phenyl, provided that when $X_1$-$X_5$ are oxygen and $R_2$, $R_4$ and $R_5$ are hydrogen, at least one of $R_1$ and $R_3$ is other than methyl;
or a methoxy-polyethyleneglycol (PEG) derivative, a pharmaceutically acceptable salt, or hydrate thereof.

33. A method of treating diabetes in a subject, comprising the step of administering to the subject a pentose derivative selected from the group consisting of
3-O-ethyl-D-xylose;
3-O-propyl-D-xylose;
1-O-methyl-D-xylose PEG;
3-O-ethyl-2,4-O-benzylidene-D-xylose-diethyl-dithioacetal;
propyl-thio-β-xylopyranoside;
lauryl-thio-β-xylopyranoside;
D-xylose-di-N-acetylcysteine-dithioacetal;
D-xylose-di-cysteine-dithioacetal;
D-xylose-diethyl-dithioacetal;
D-xylose-dipropyl-dithioacetal;
1,3-O-dimethylxylopyranoside;
2,4-benzylidene-D-xylose-diethyl-dithioacetal;
3-O-methyl-2,4-O-benzylidene-D-xylose-diethyl-dithioacetal;
3-O-propyl-2,4-O-benzylidene-D-xylose-diethyl-dithioacetal;
3-O-ethyl-5-O-benzoyl-D-xylose-diethyl-dithioacetal;
3-O-propyl-1,2-benzylidene-D-xylose; and
3-O-propyl-2,4-benzylidene-D-xylose;
in an amount effective to lower blood glucose levels in the subject, thereby treating diabetes in the subject.

* * * * *